United States Patent [19]

McKinney et al.

[11] Patent Number: 5,328,822
[45] Date of Patent: Jul. 12, 1994

[54] APPARATUS AND METHOD FOR SEDIMENTATION BASED BLOOD ANALYSIS

[75] Inventors: David K. McKinney; Milton E. Fuller; Berry V. Carone, all of Reno, Nev.

[73] Assignee: Solid State Farms, Inc., Reno, Nev.

[21] Appl. No.: 512,845

[22] Filed: Apr. 23, 1990

[51] Int. Cl.$^5$ .......................... C12Q 1/00; C12M 1/00; G01J 1/20; G01N 33/48
[52] U.S. Cl. ............................................. 435/4; 73/3; 250/203.1; 250/203.2; 250/330; 250/333; 250/334; 250/461.2; 346/33 A; 356/39; 356/40; 435/7.21; 435/287; 435/289; 435/291
[58] Field of Search ................... 73/3; 436/70; 356/39, 356/40; 250/333, 334, 330, 203.1, 203.2, 222.2, 461.2; 346/33 A; 435/4, 7.21, 287, 289, 291

[56] References Cited

U.S. PATENT DOCUMENTS

| | | |
|---|---|---|
| 2,725,782 | 12/1955 | Worley . |
| 2,982,170 | 5/1961 | Wyss . |
| 3,261,256 | 7/1966 | Morton, Jr. . |
| 3,288,019 | 11/1966 | Blumenfeld . |
| 3,422,443 | 1/1969 | Jansen ................................. 346/107 |
| 3,474,458 | 10/1969 | Standaart ............................ 346/107 |
| 3,604,924 | 9/1971 | Standaart ...................... 346/33 ME |
| 3,631,513 | 12/1971 | Fotsch ................................. 346/107 |
| 3,715,761 | 2/1973 | Drekter et al. .................... 346/33 A |
| 3,844,662 | 10/1974 | Froreich ................................ 356/246 |
| 3,952,579 | 4/1976 | Nakajima ............................ 73/61.4 |
| 4,041,502 | 8/1977 | Williams et al. ................. 346/33 A |
| 4,118,974 | 10/1978 | Nozaki et al. ......................... 73/61.4 |
| 4,848,900 | 7/1989 | Kuo ..................................... 356/39 |

OTHER PUBLICATIONS

"The Age-Related Hemorheological and Osmotic Properties of Human Blood," by Cerny et al., Biorheology, vol. 74, No. 182, pp. 85-89 (1978).
"The Erythrocyte Sedimentation Rate of Blood Reconsidered," by Merrill et al., Biorheology, vol. 74, No. 182, pp. 90-95 (1978).
"Optical Method for Haematocrit Determination," by Singh et al., Medical & Biological Engineering & Computing, Vo. 20, pp. 527-528 (Jul., 1982).
"The Erythrocyte Sedimentation Rate Time Curve: Critique of an Established Solution," by Dorrington et al., Biomechanics, vol. 16, No. 1, pp. 99-100 (1983).
"Erythrocyte Sedimentation Rate—From Folklore to Facts," by Bedell et al., The American Journal of Medicine, vol. 78, pp. 1001-1009 (Jun., 1985).

Primary Examiner—Michael G. Wityshyn
Assistant Examiner—Jane A. Williams
Attorney, Agent, or Firm—Flehr, Hohbach, Test, Albritton & Herbert

[57] ABSTRACT

An apparatus and process for accurately determining settling data for the settling of erythrocyte cells from a plasma fluid in a test specimen of blood. The apparatus includes a settling tube, a sensing assembly movably mounted proximate the settling tube. Preferably an infrared emitter and detector are provided in the sensing assembly, and a control assembly is provided which senses data at a high rate and is responsive to the sensed data to sample or store the time at which sensed reflectivity exceeds a threshold level. When the threshold is reached, data is sampled and the tracking head is moved by a very small step. This process is repeated to enable tracking of the descent of the separation boundary between the erythrocyte cells and plasma fluid. The apparatus senses changes in reflectivity of the erythrocyte portion of the specimen below and up to the separation boundary. The apparatus and process also includes a scanning process to calibrate the reflectivity for each test specimen, the reflectivity also is measured immediately after moving the sensing assembly and recorded as a function of the position of the sensing assembly. An apparatus and process for scanning the plasma fluid and white cells above the separation boundary for reflectivity of infrared or visible light radiation as a function of height above the separation boundary also is disclosed.

30 Claims, 24 Drawing Sheets

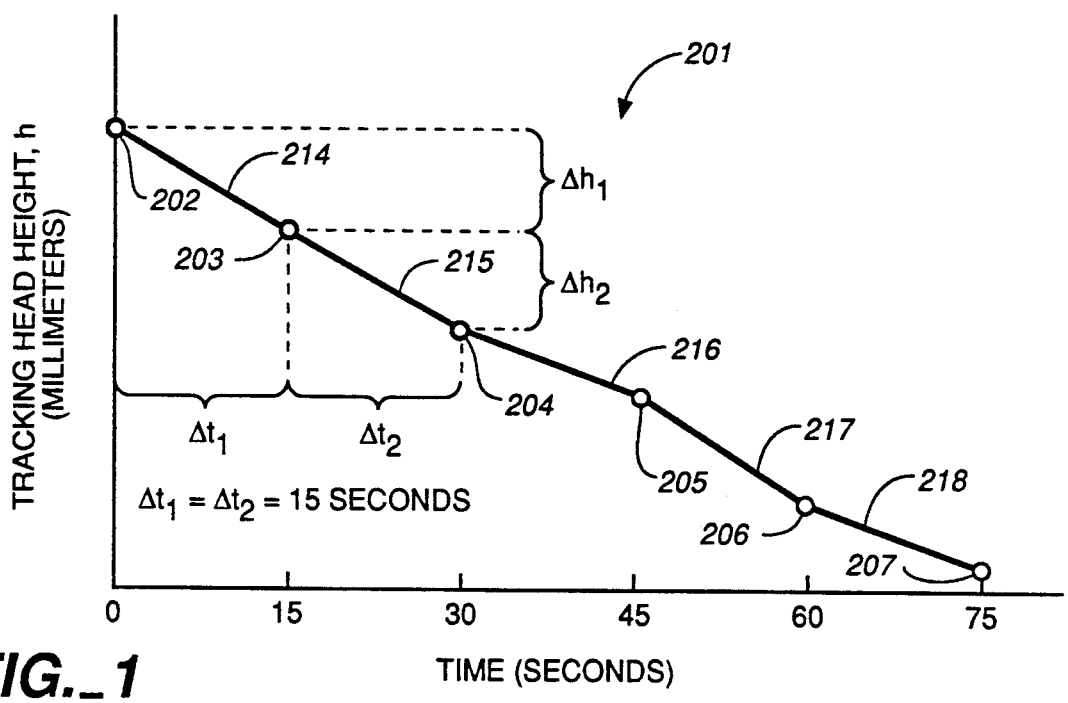
FIG._1
(PRIOR ART)
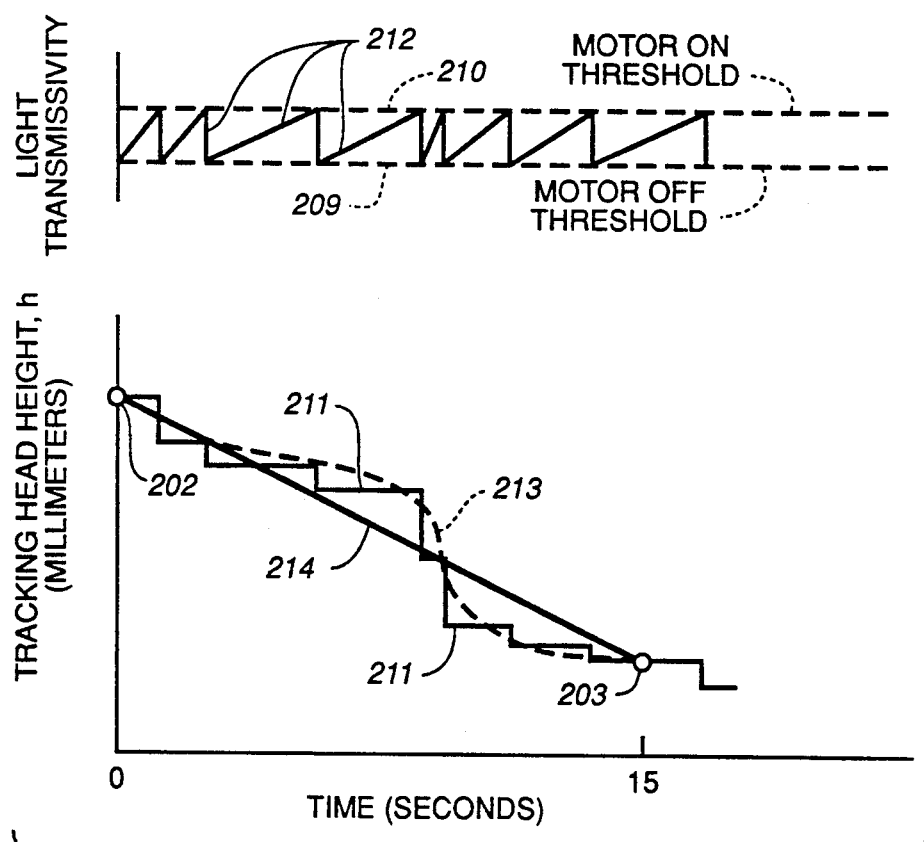
FIG._2
(PRIOR ART)

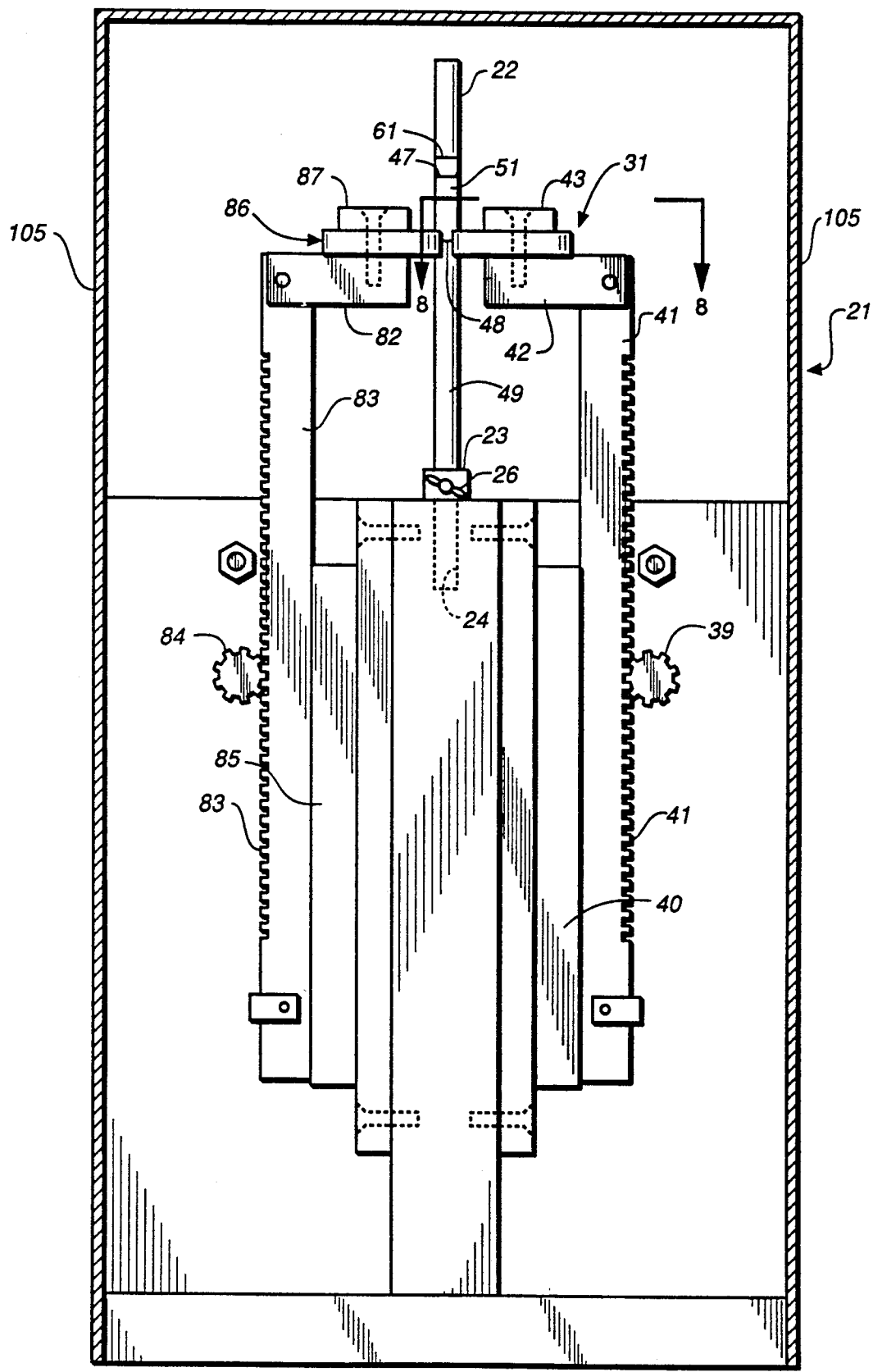
FIG._3

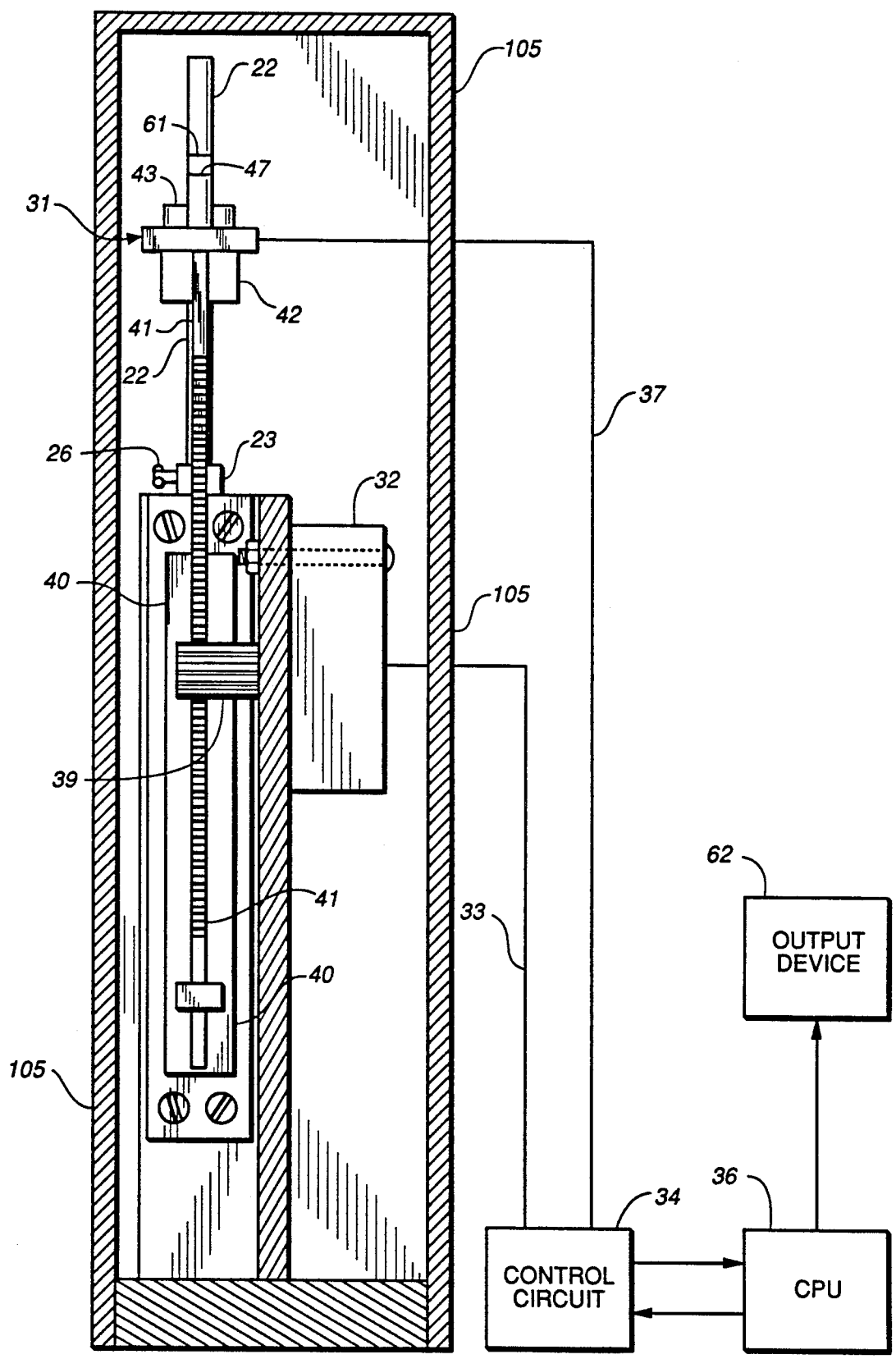
FIG._4

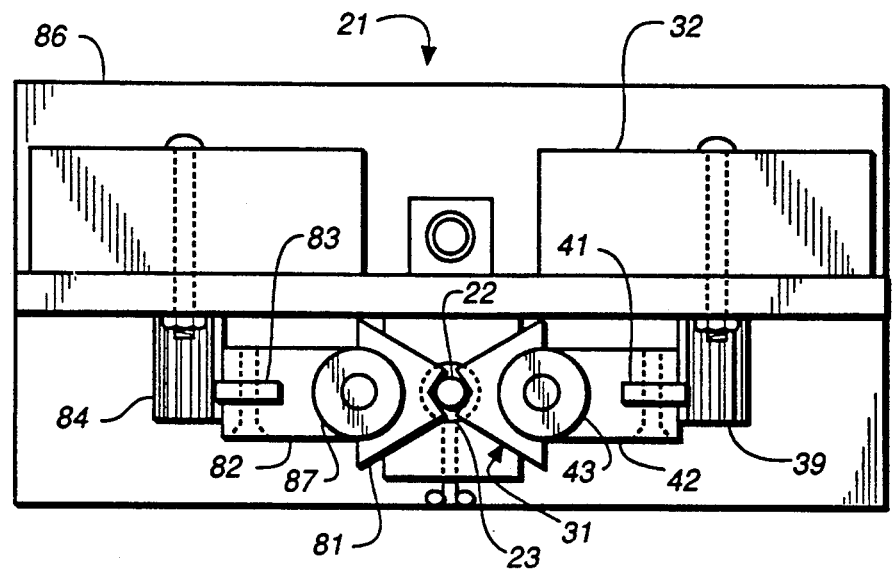
FIG._5
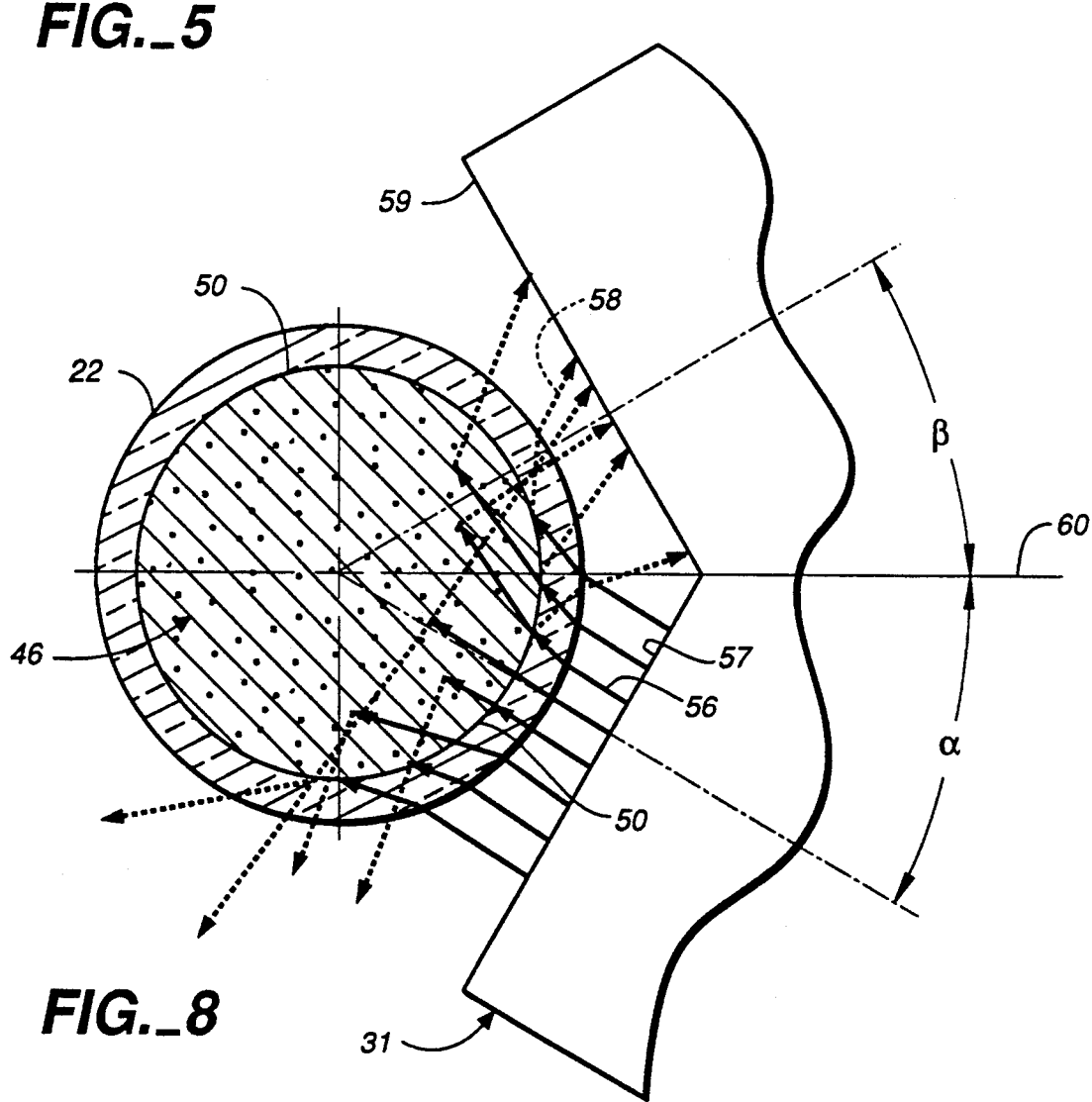
FIG._8

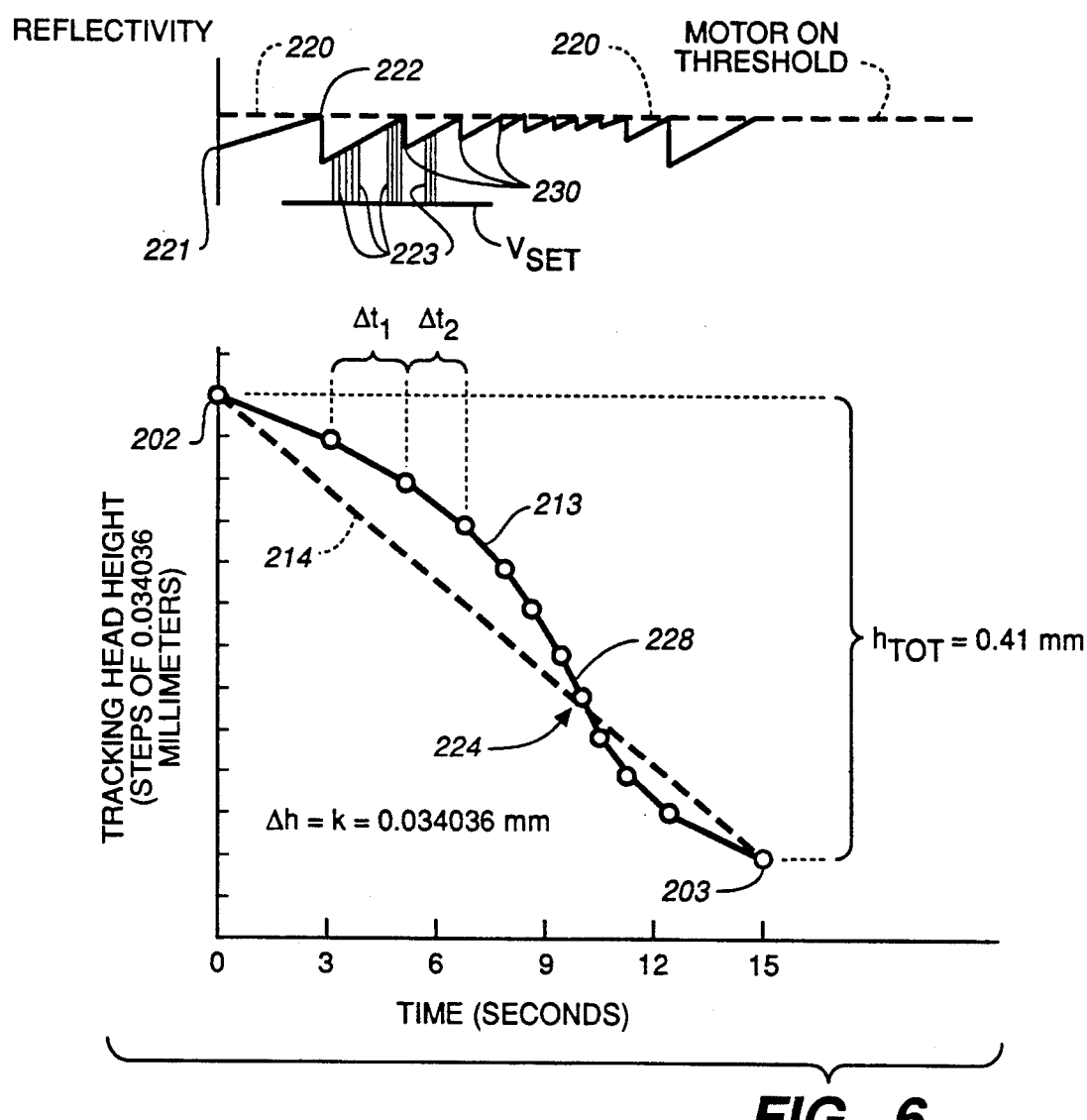
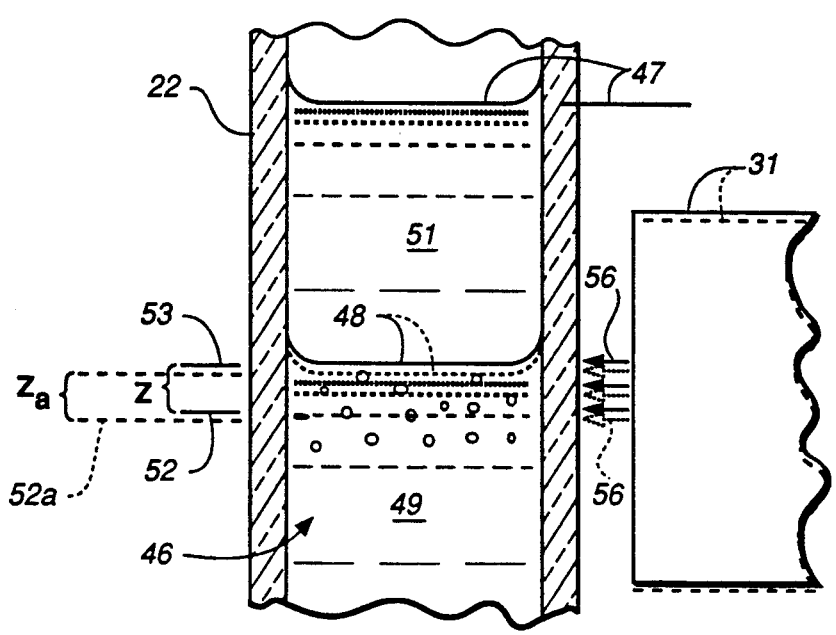
FIG._6
FIG._7

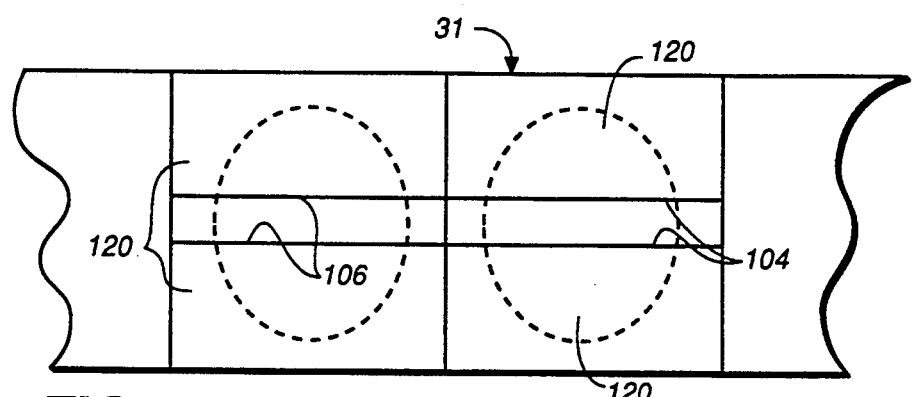
FIG._9
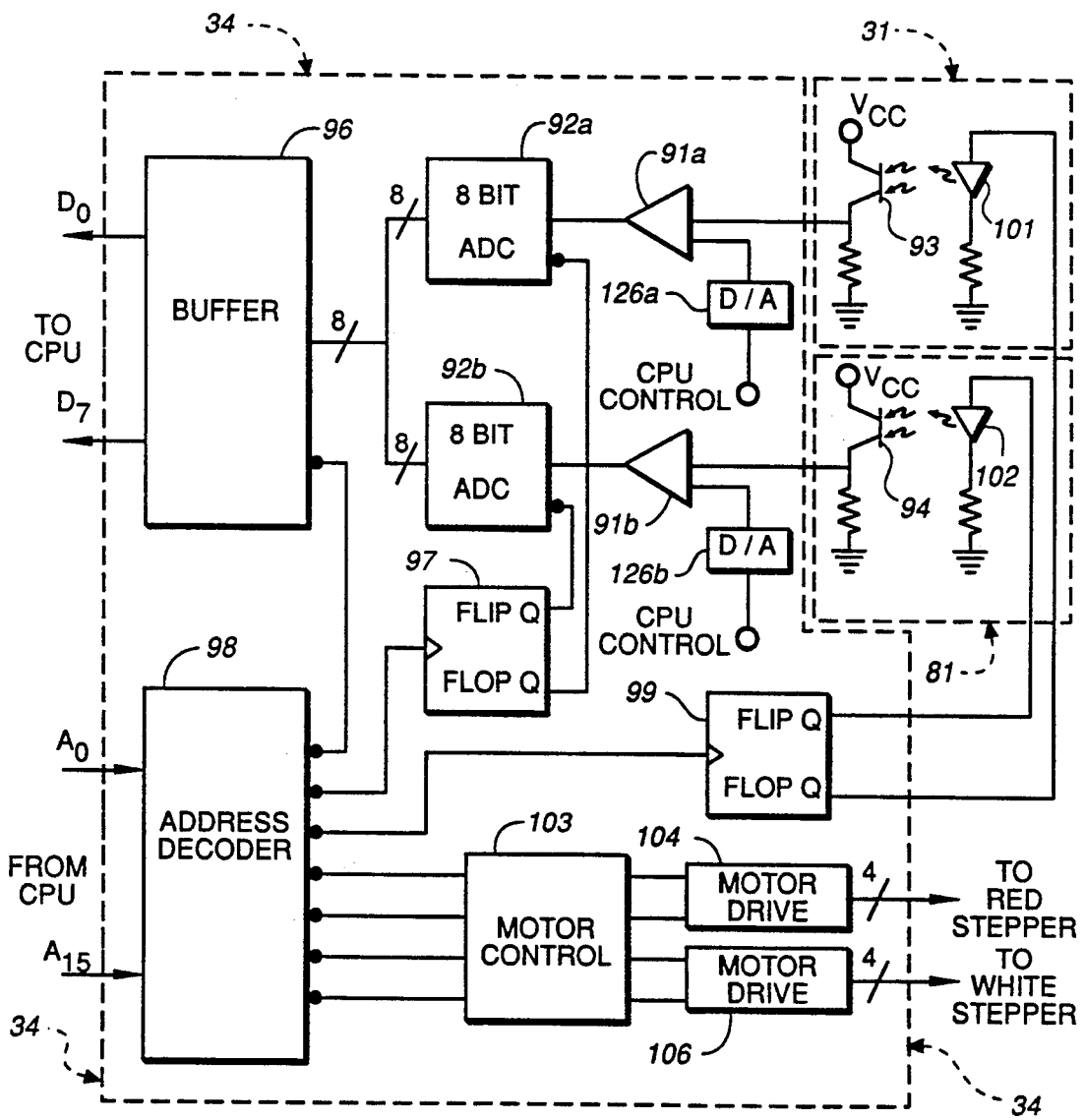
FIG._10

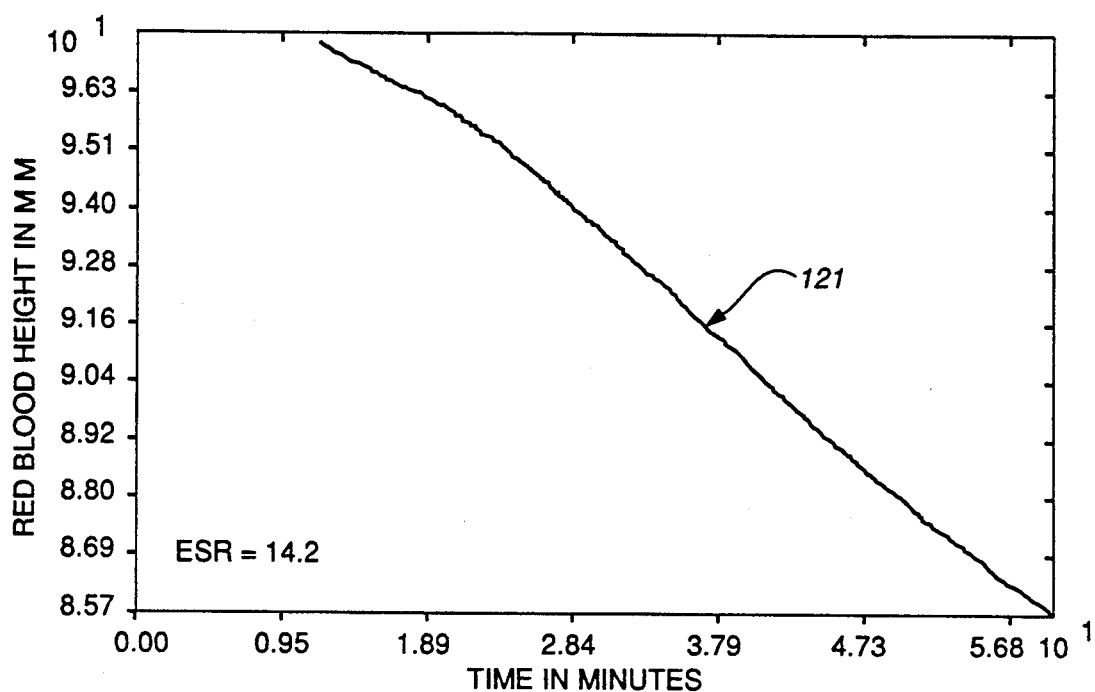
FIG._11A
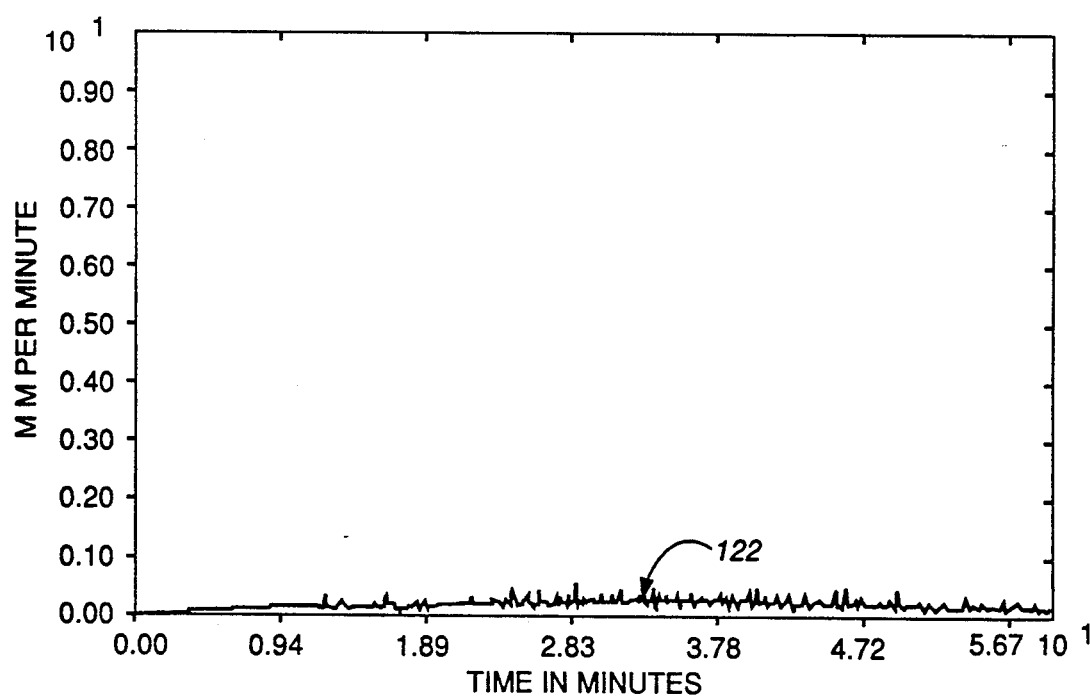
FIG._11B

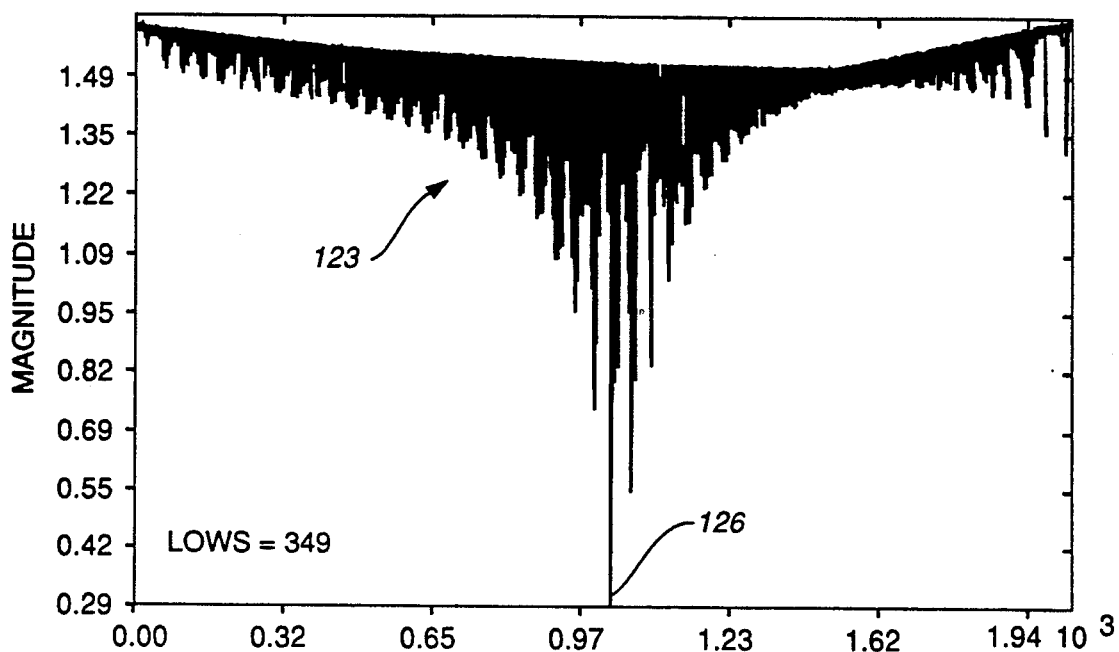
FIG._11C
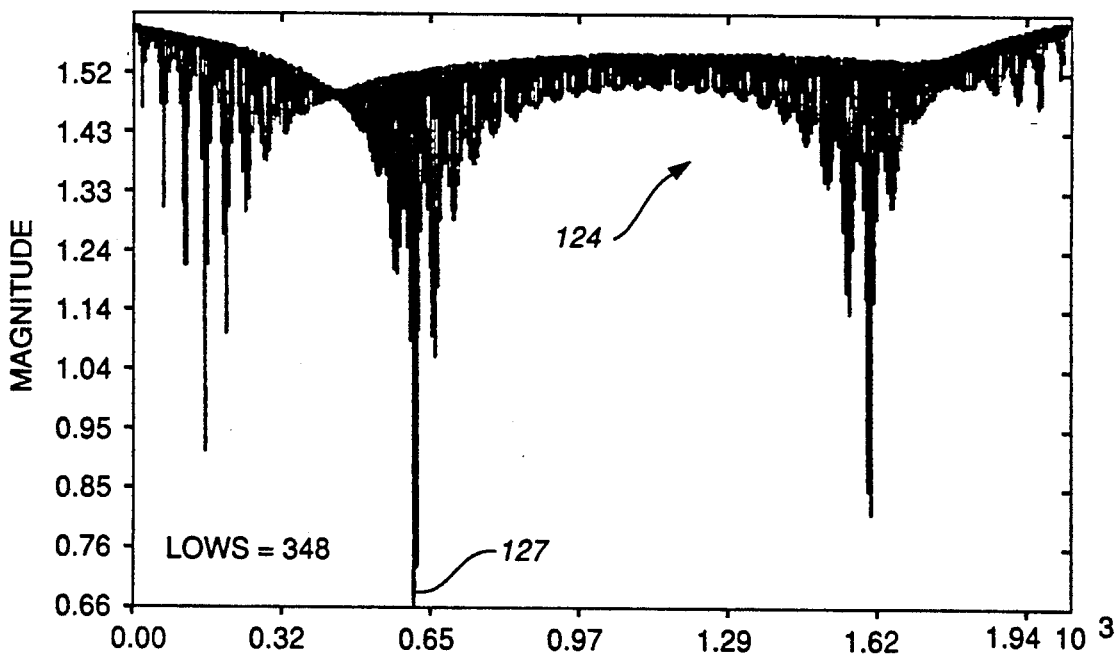
FIG._11D

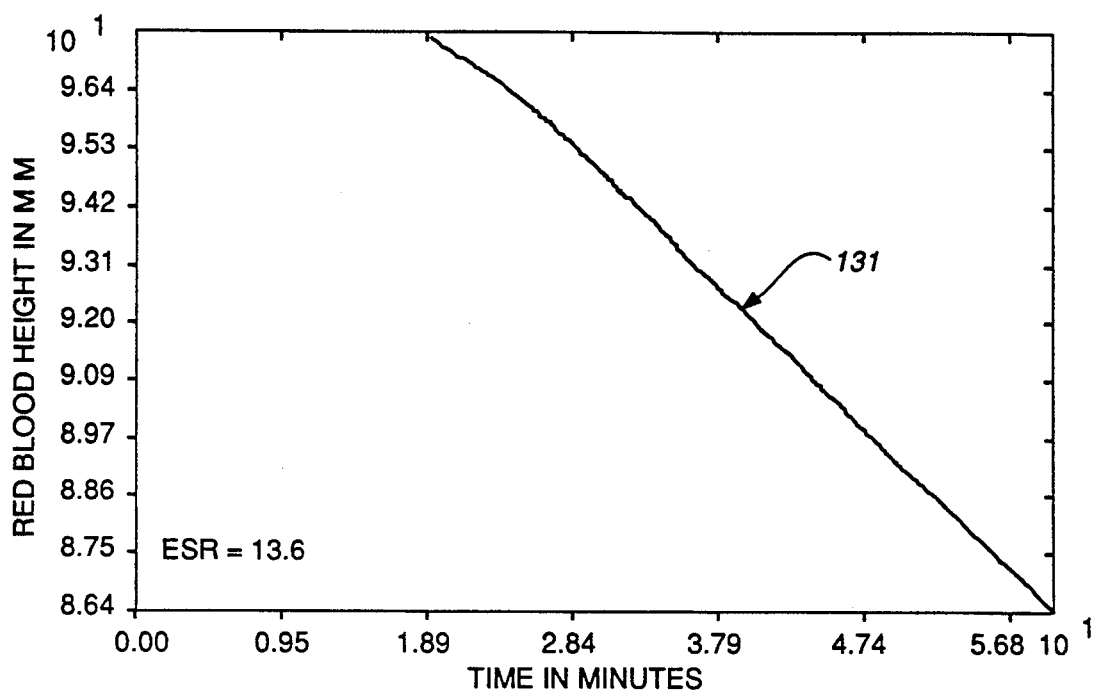
FIG._12A
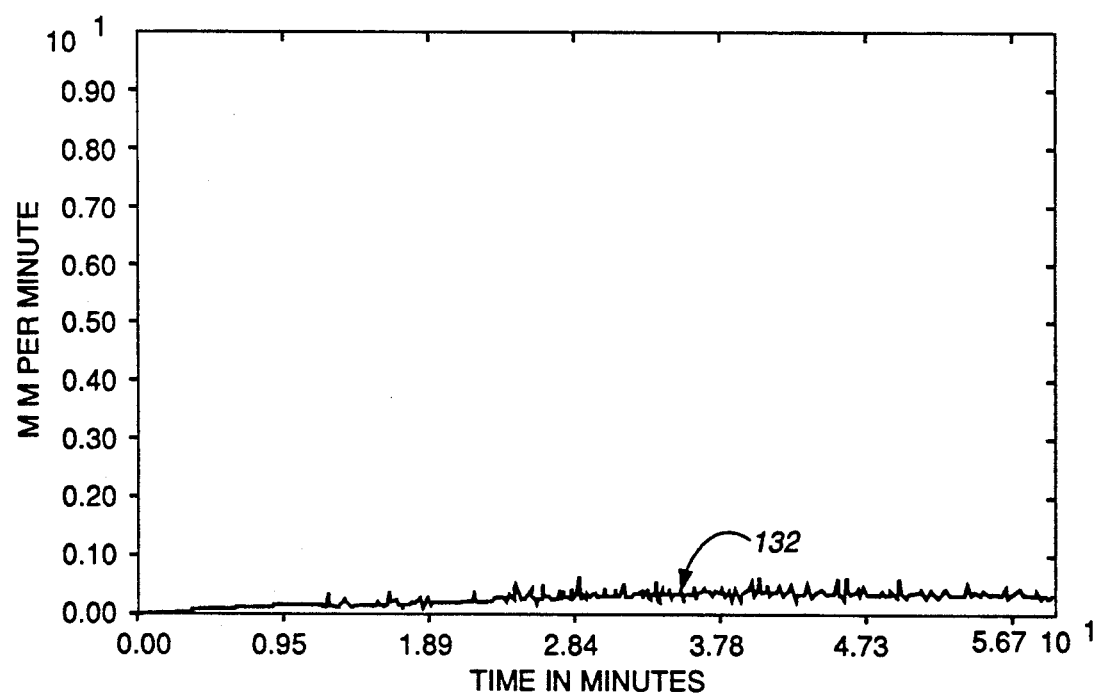
FIG._12B

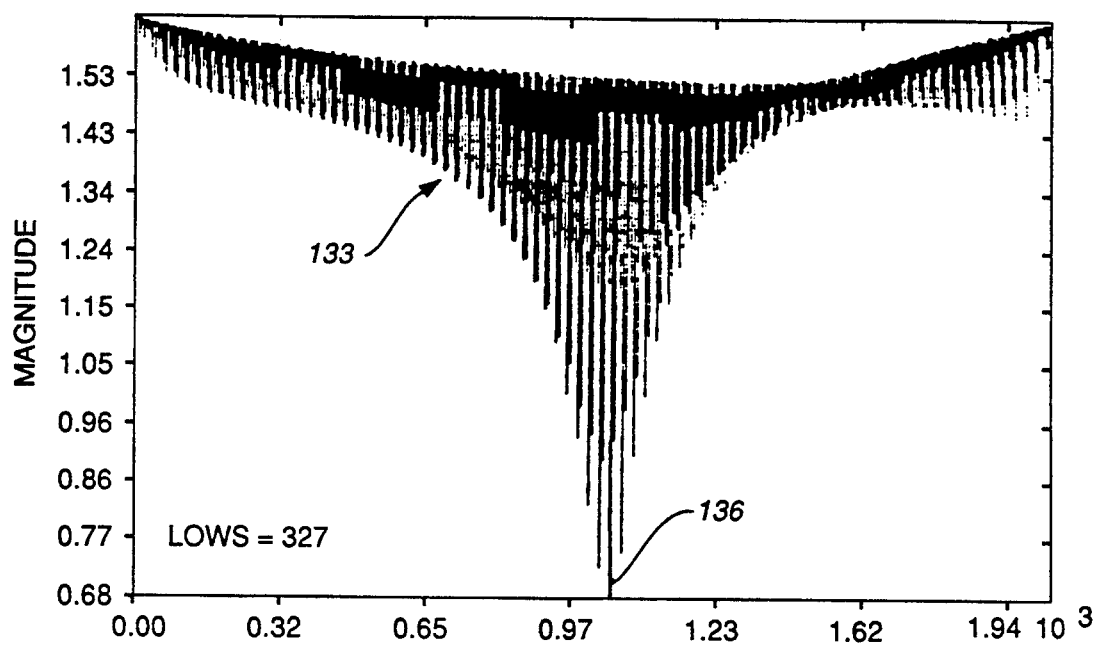
FIG._12C
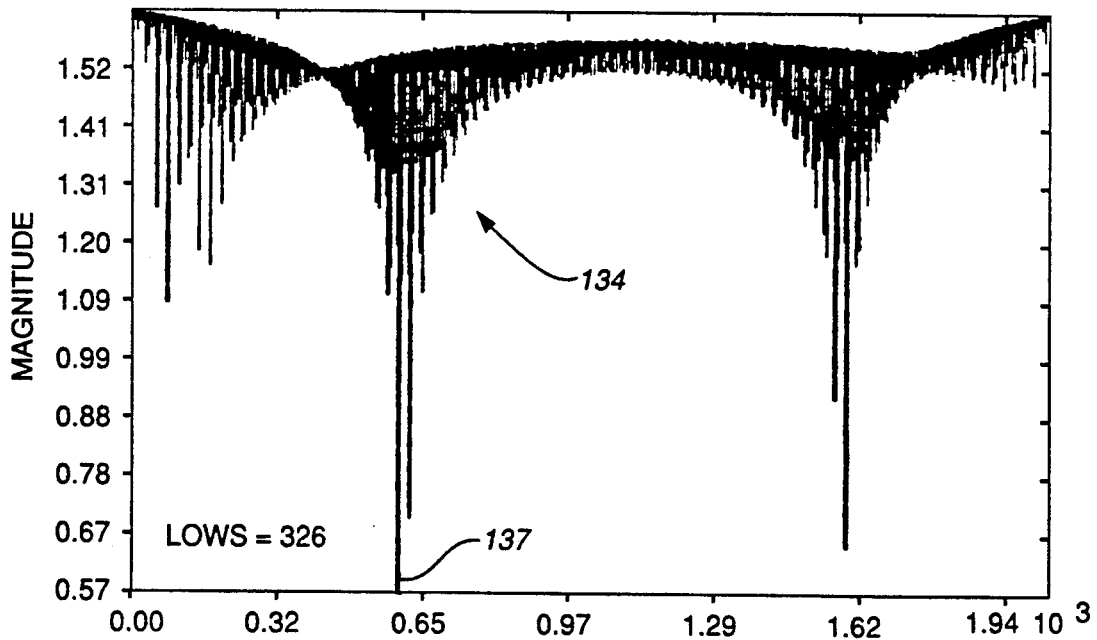
FIG._12D

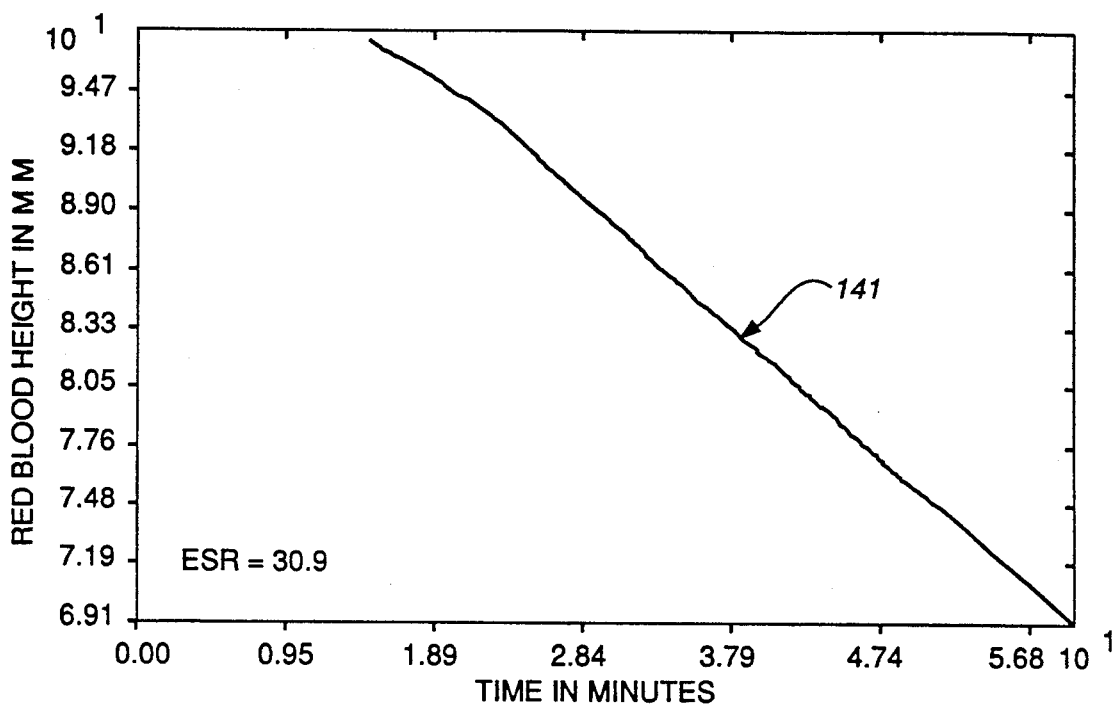
FIG._13
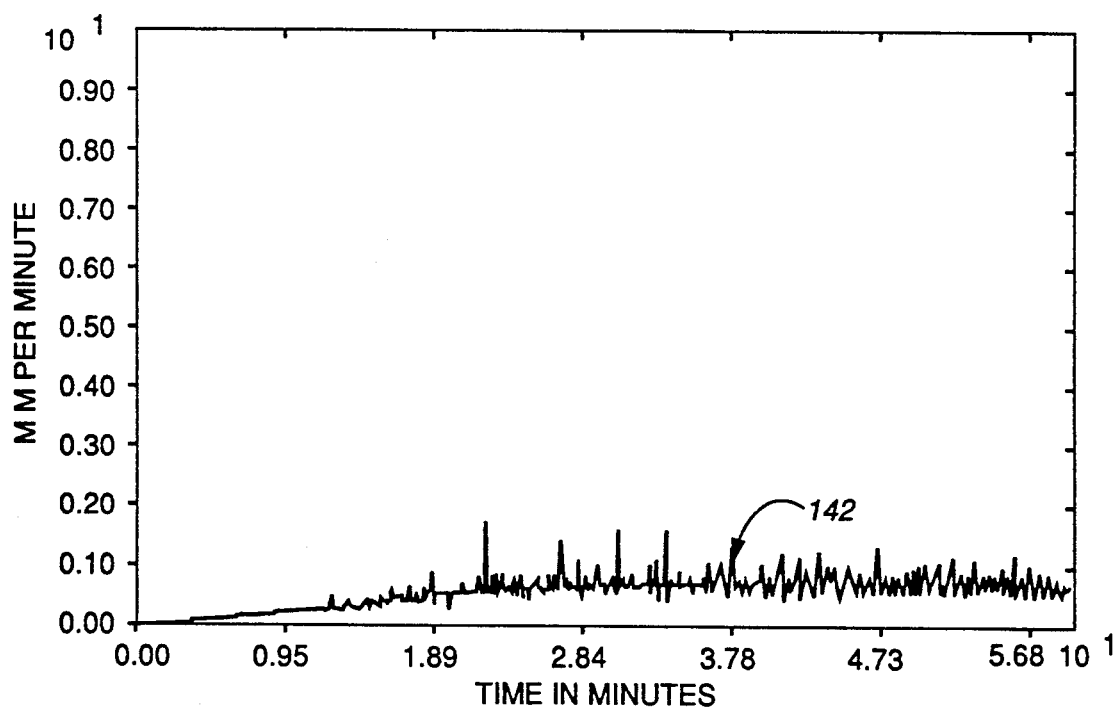
FIG._14

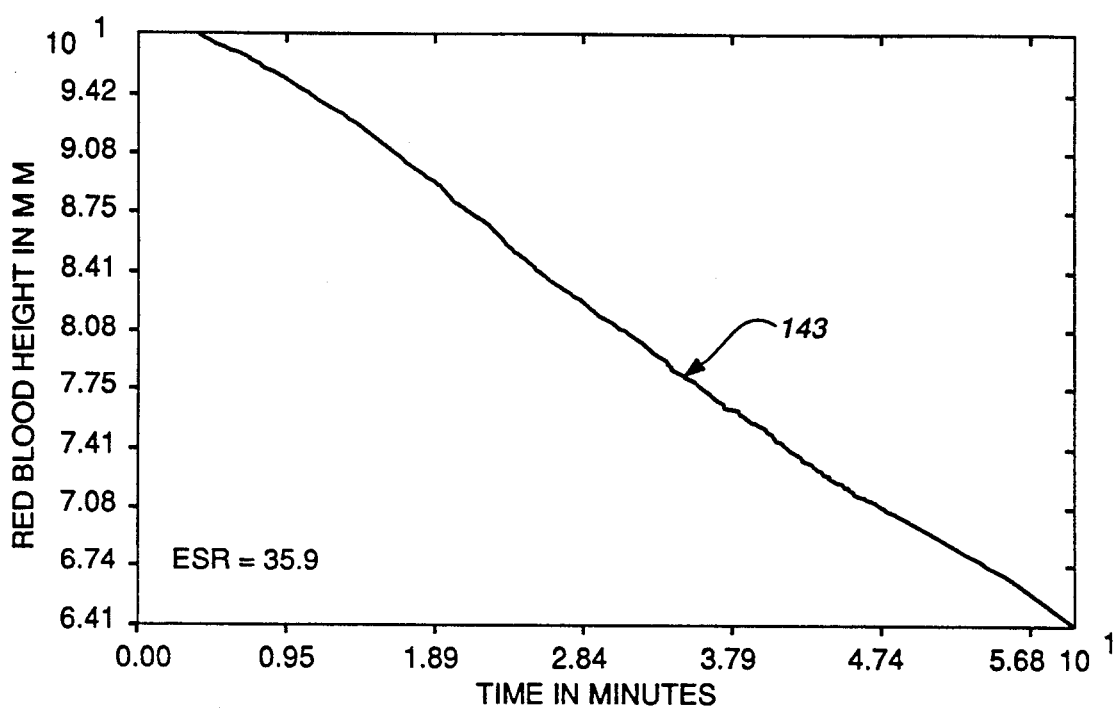
FIG._15A
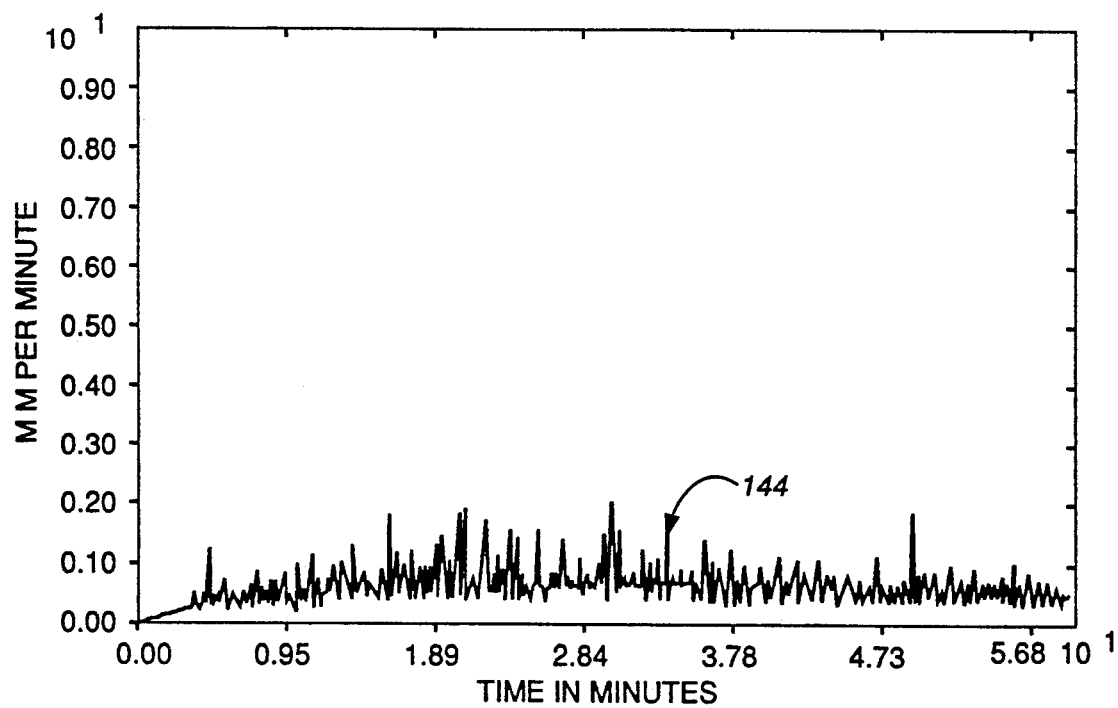
FIG._15B

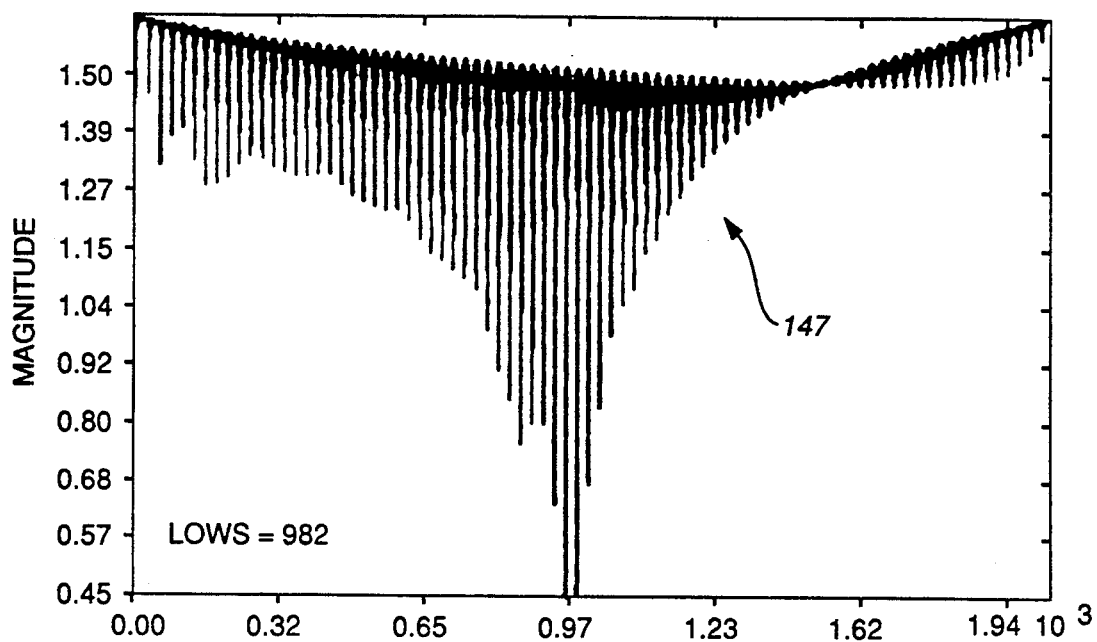
FIG._15C
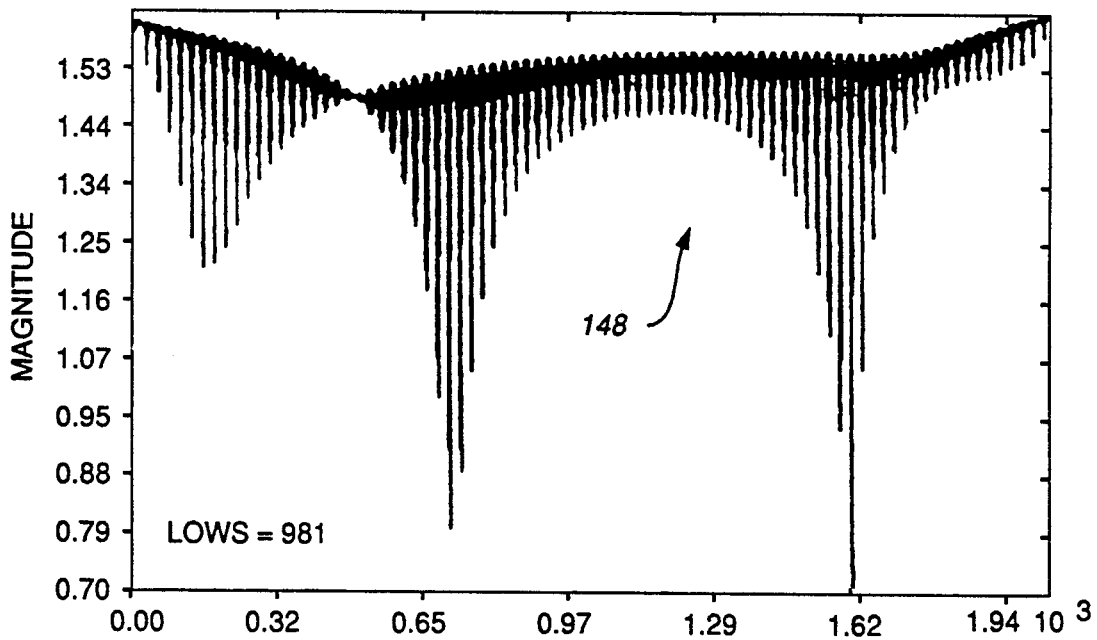
FIG._15D

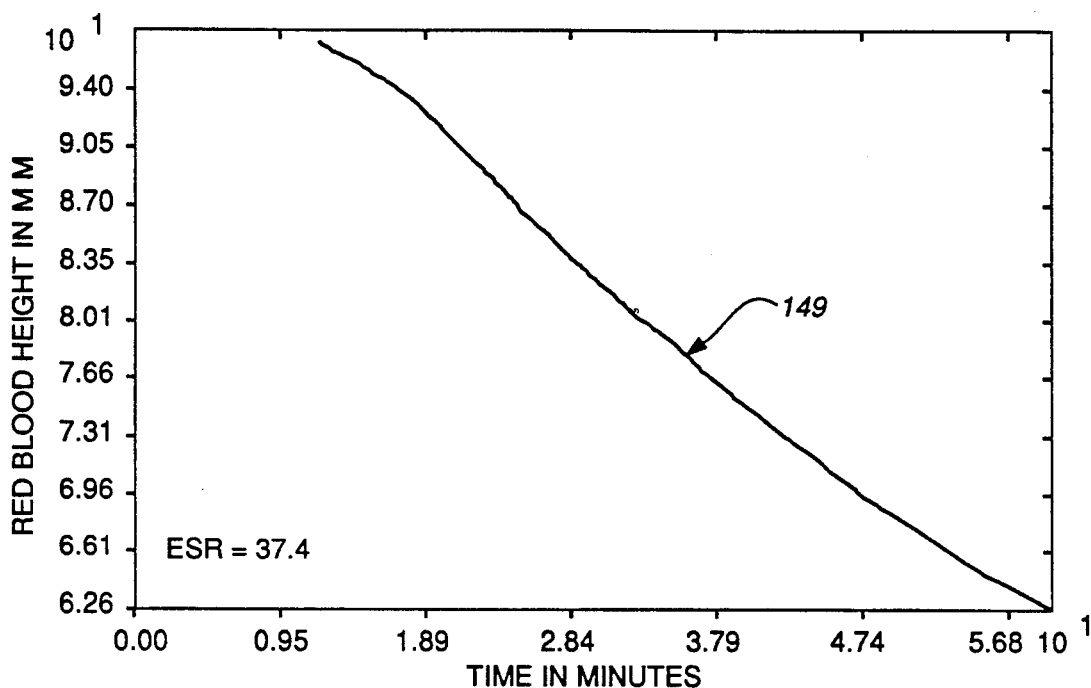
FIG._16A
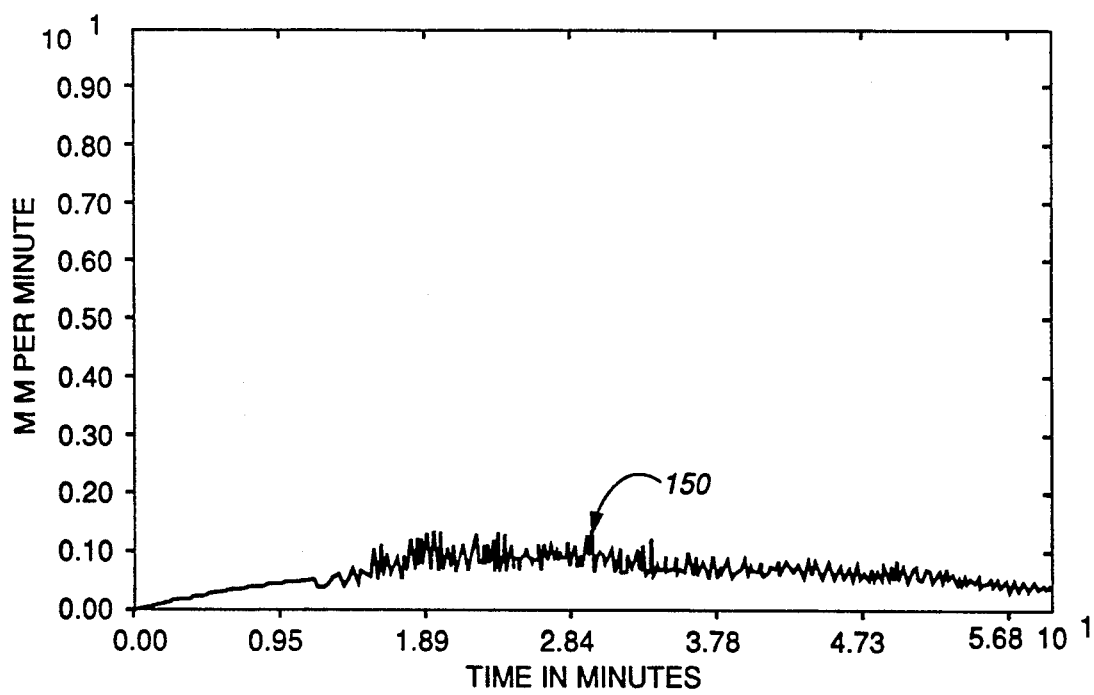
FIG._16B

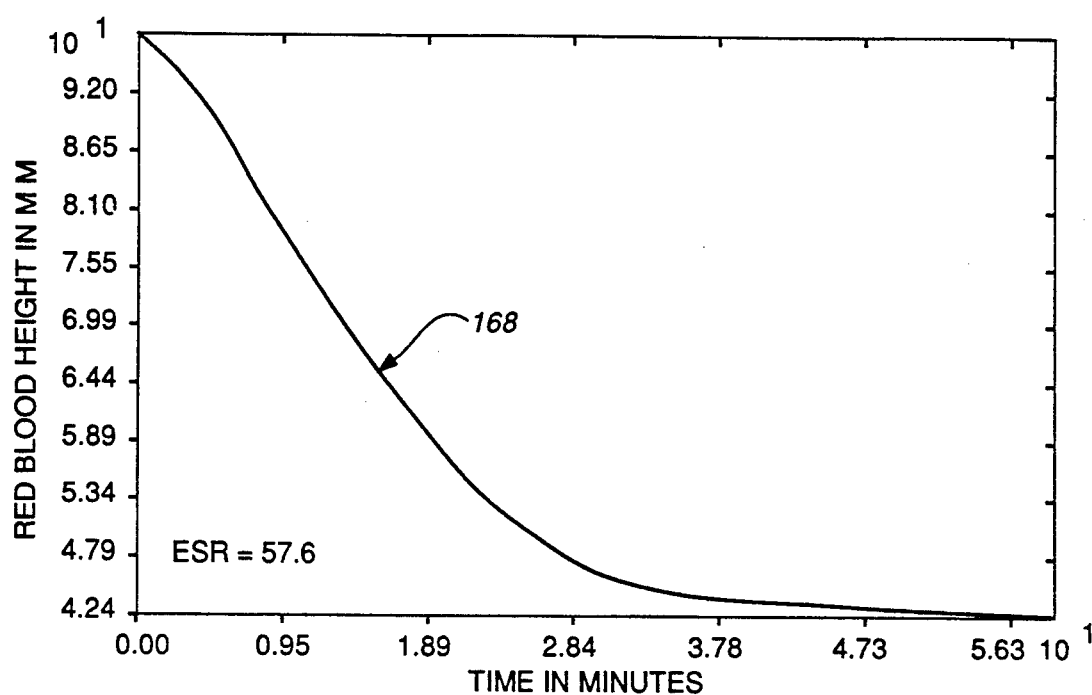
FIG._17A
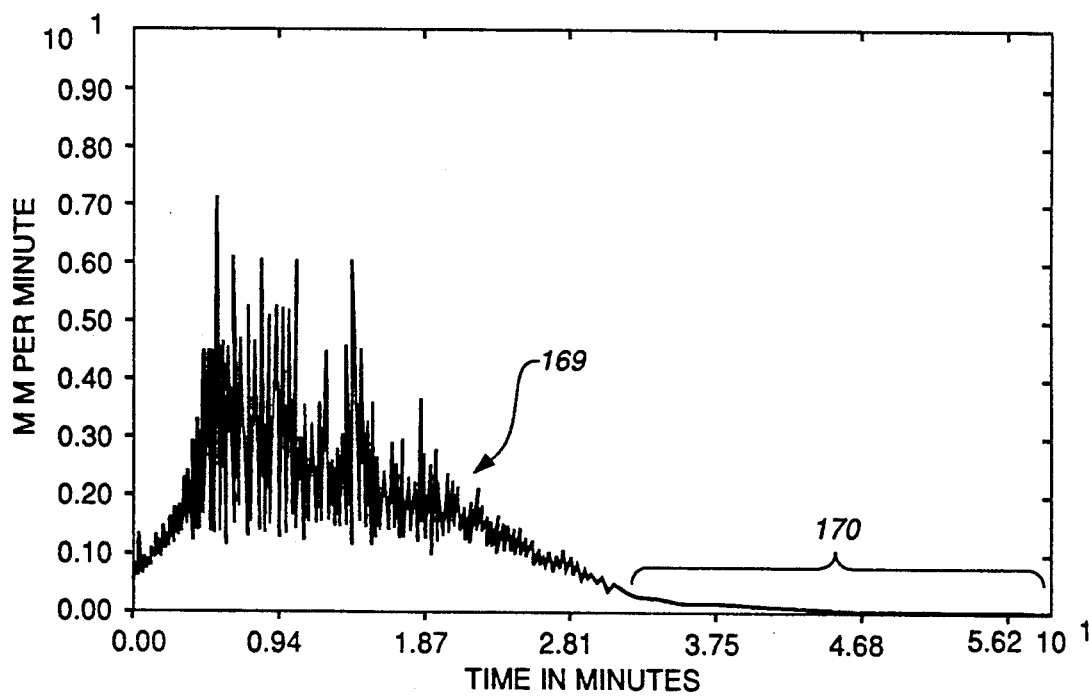
FIG._17B

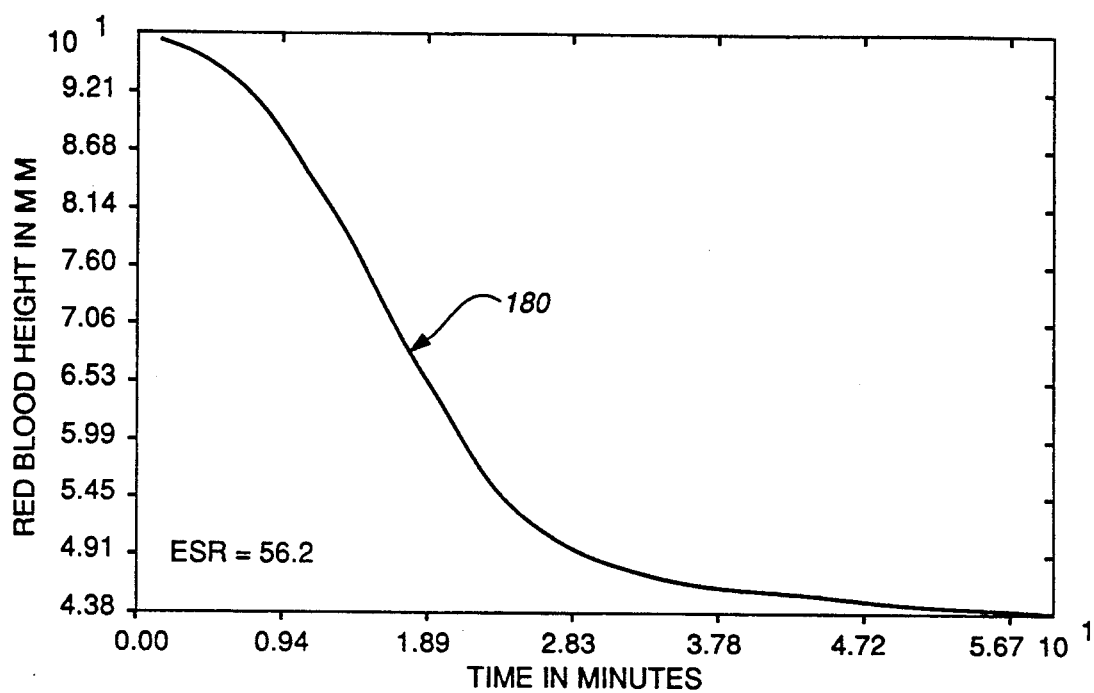
FIG._18A
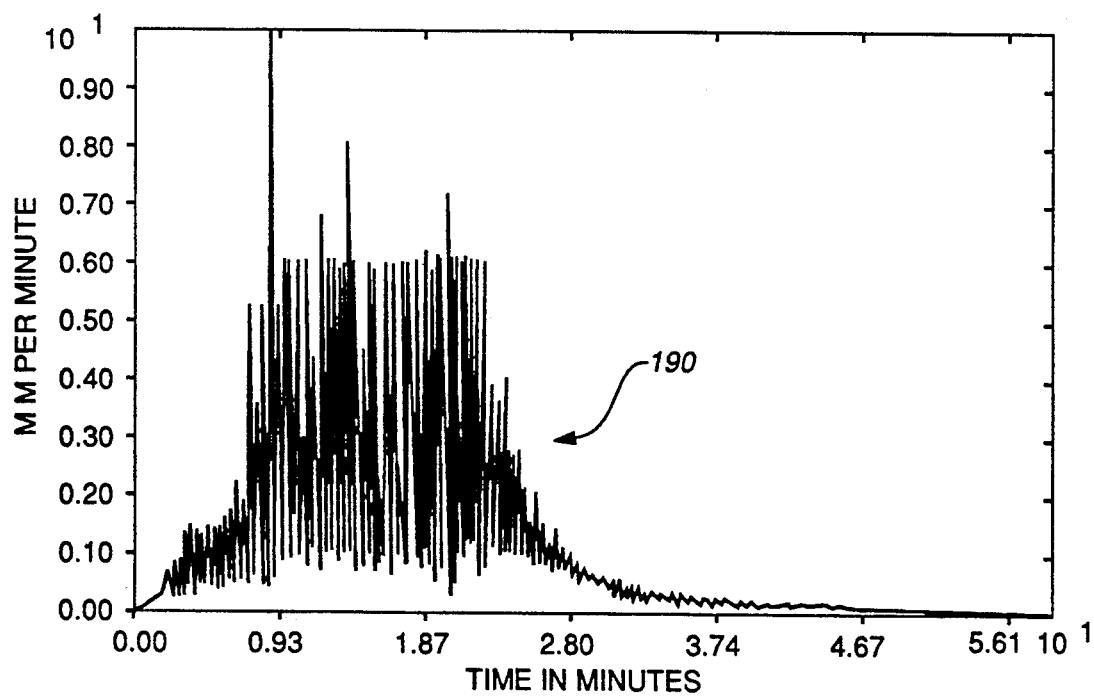
FIG._18B

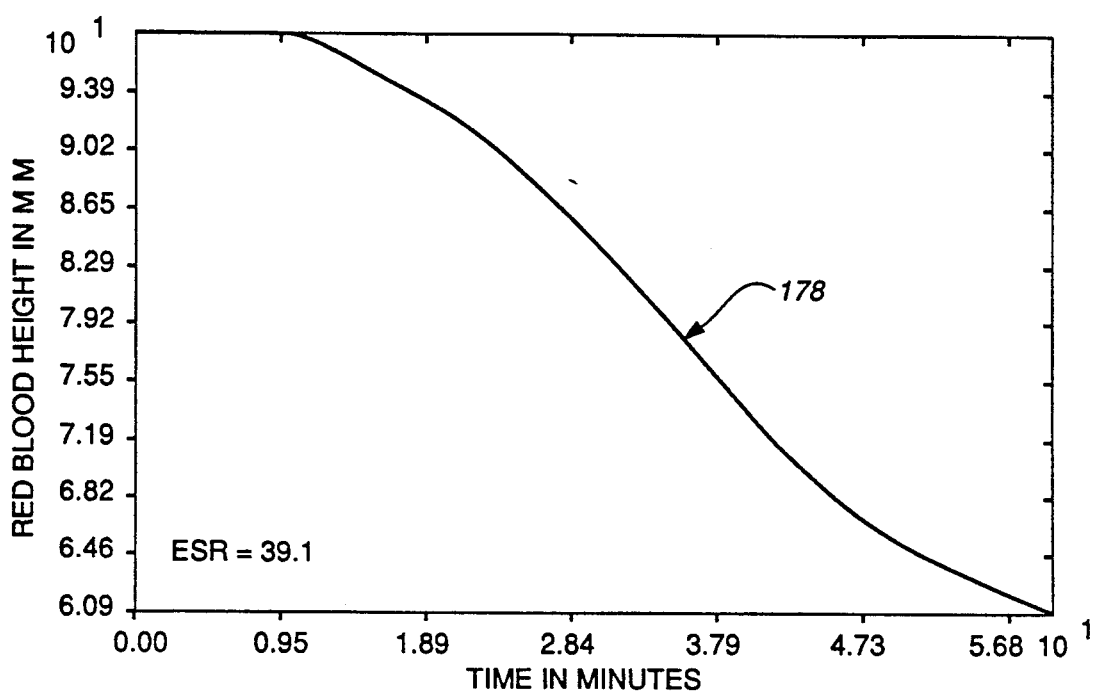
FIG._19A
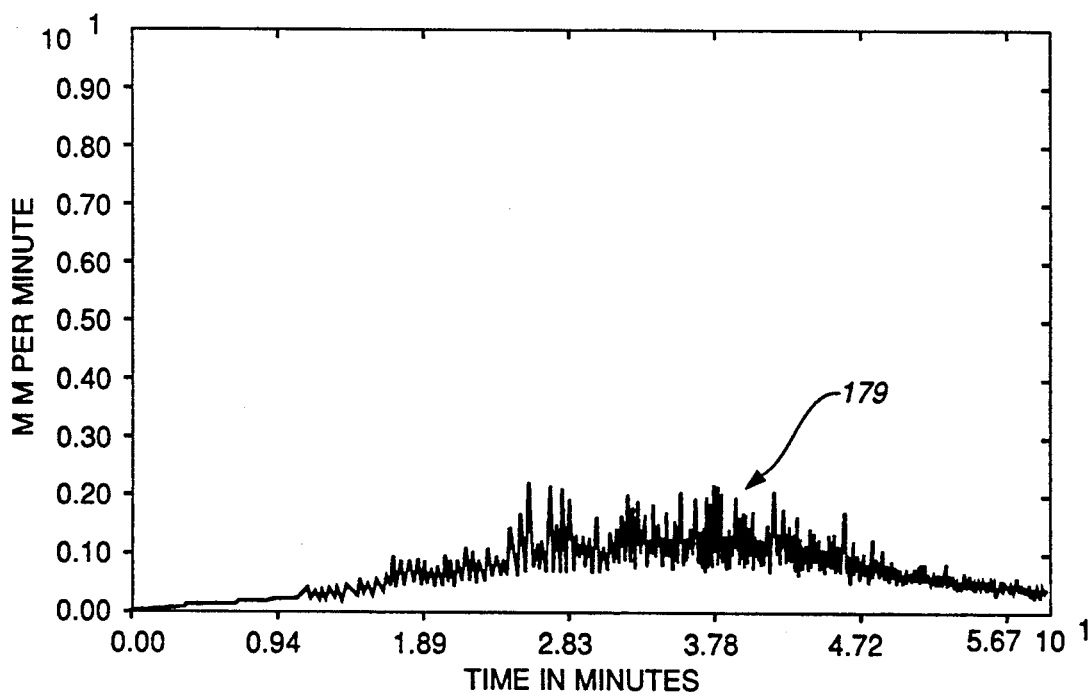
FIG._19B

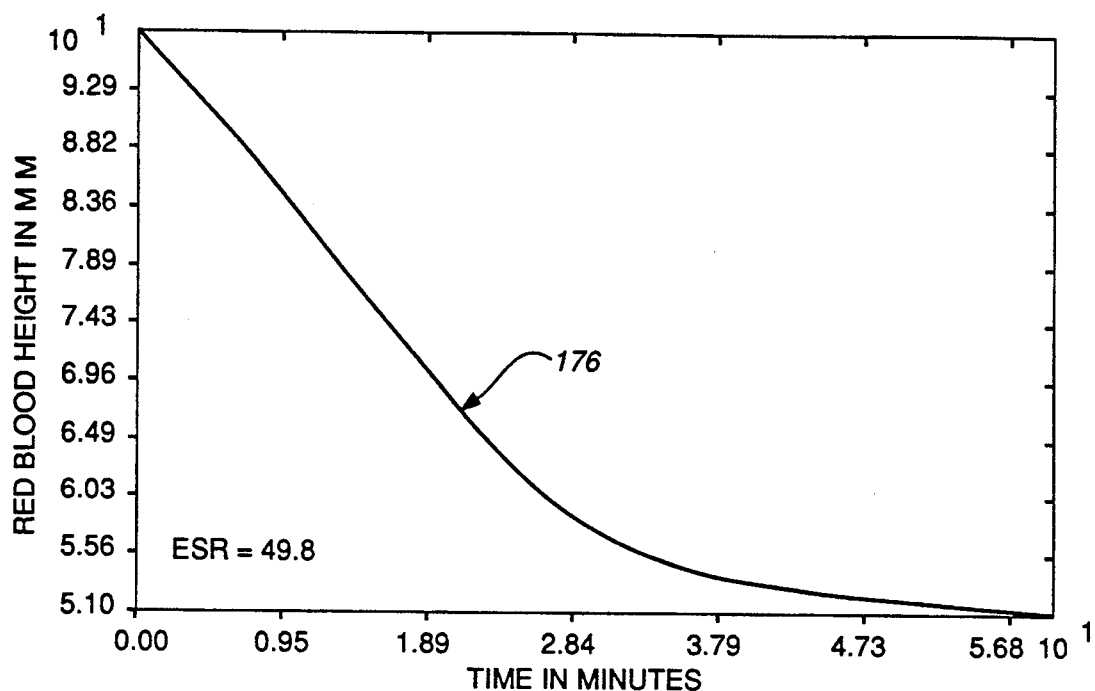
FIG._20A
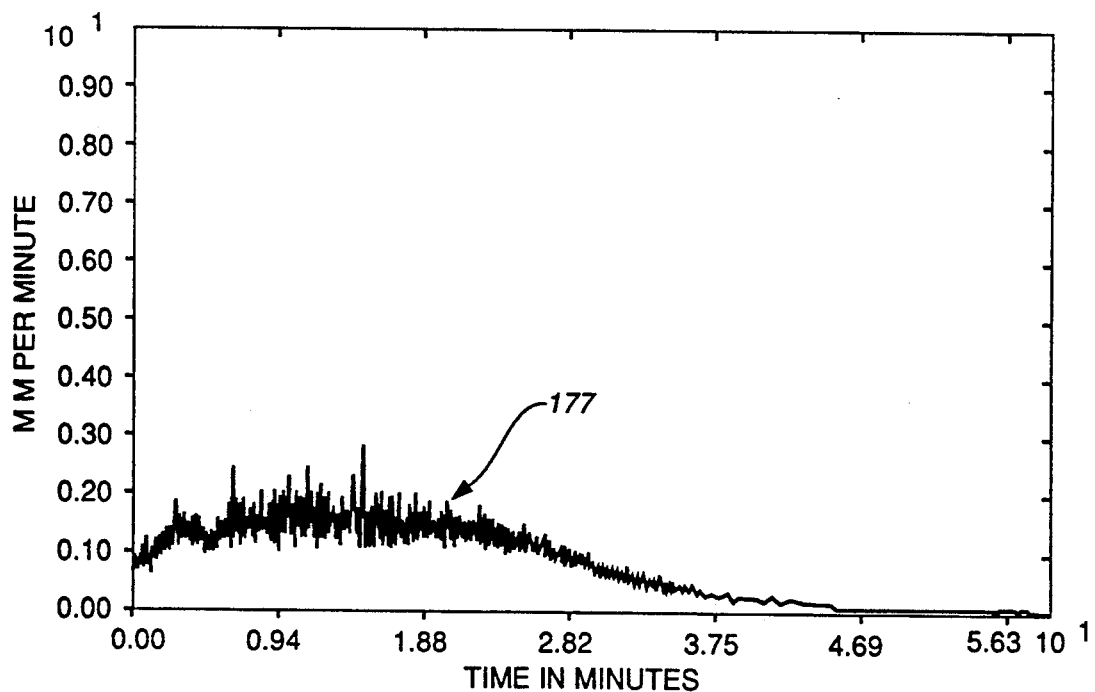
FIG._20B

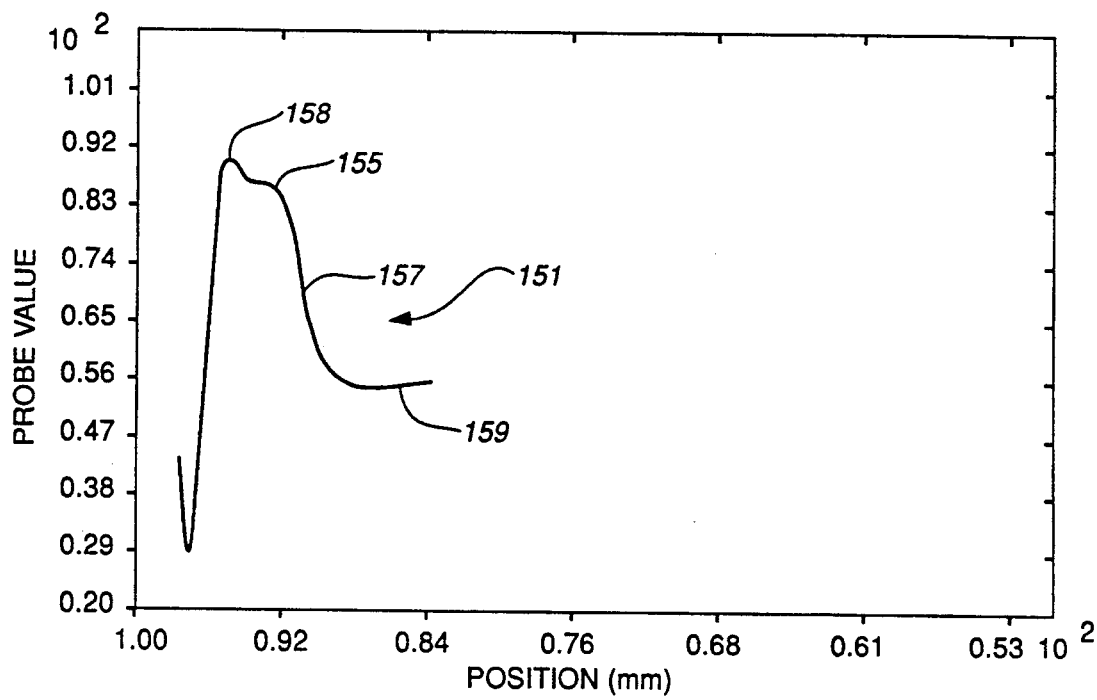
FIG._21
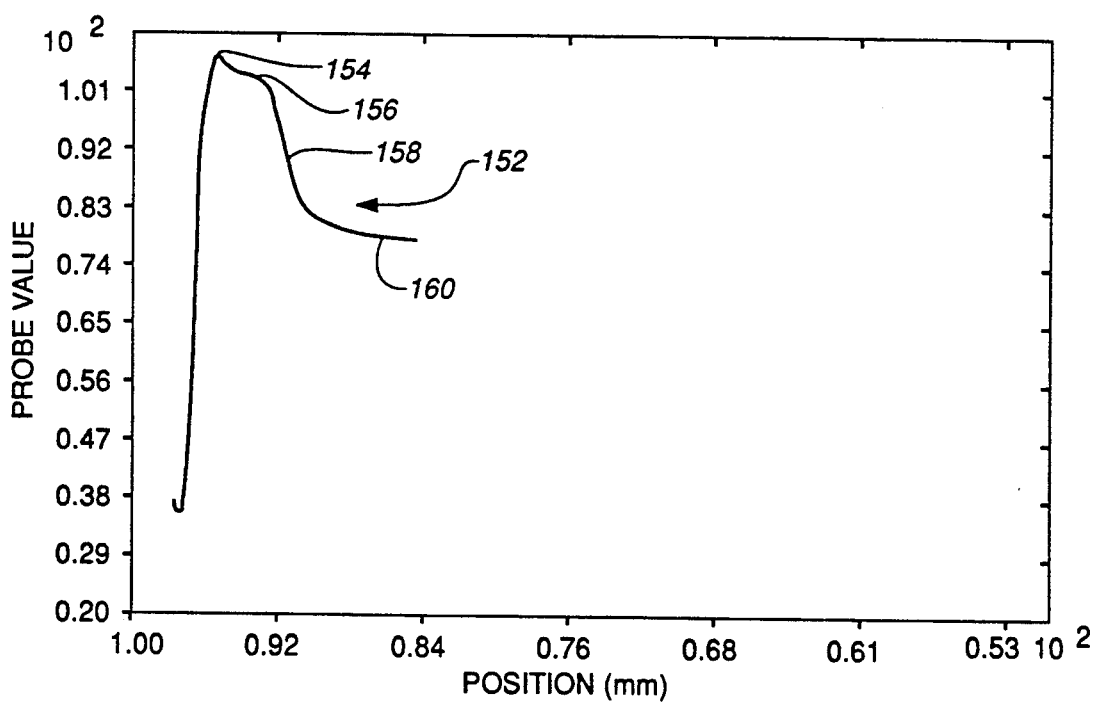
FIG._22

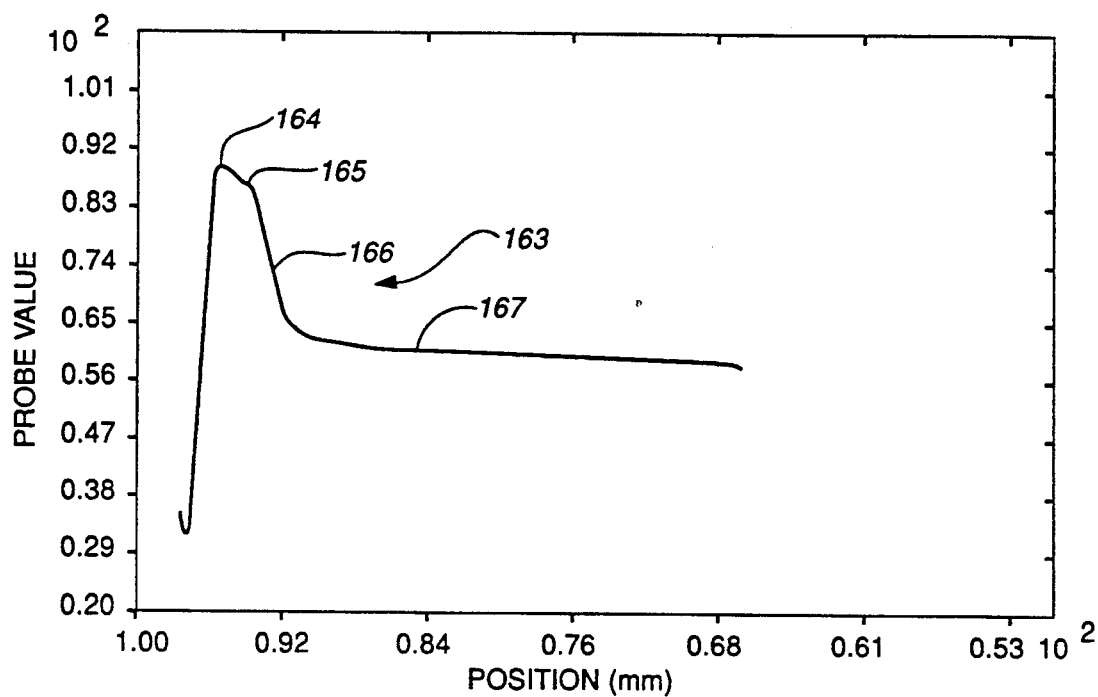
FIG._23
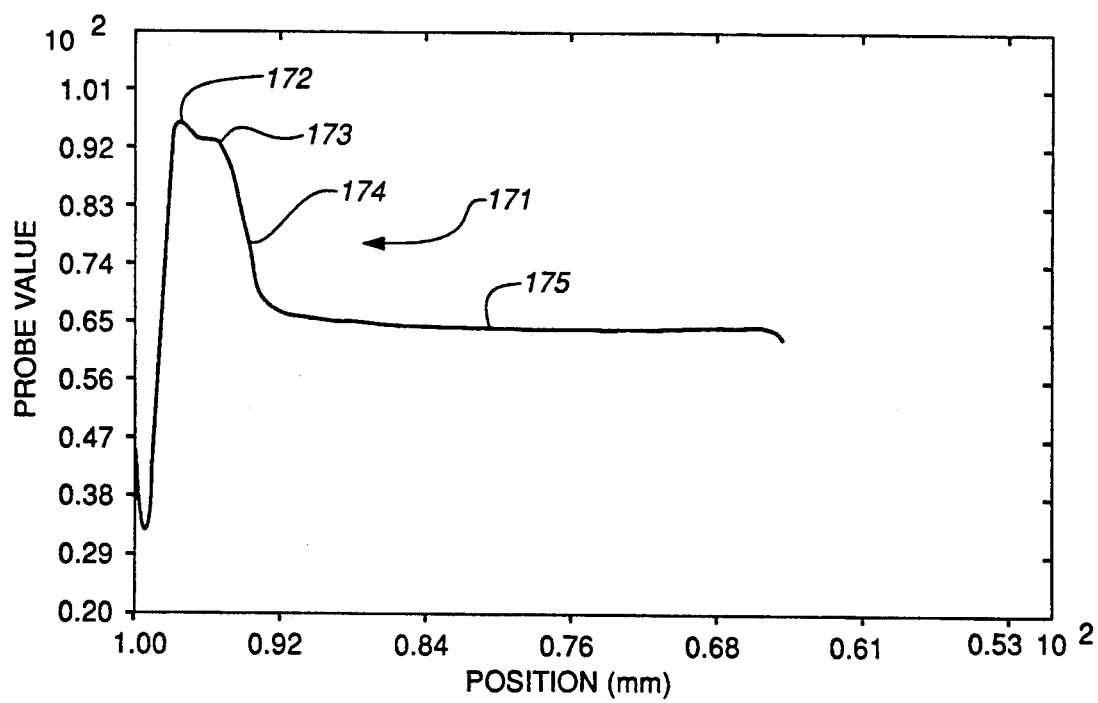
FIG._24

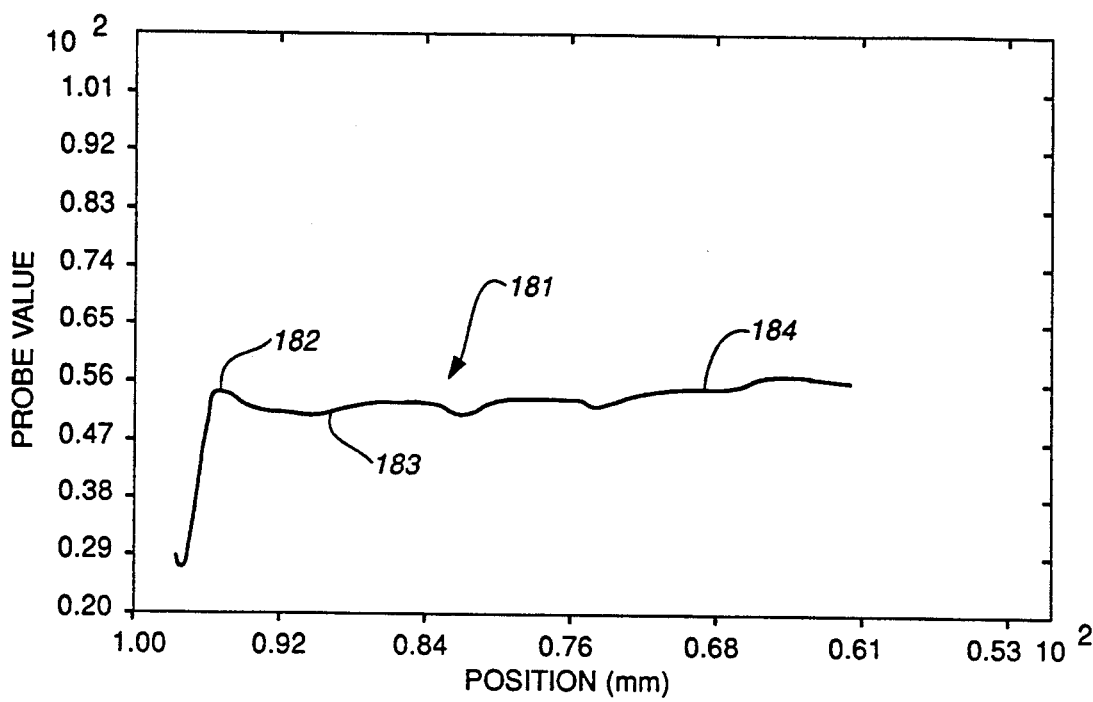
FIG._25
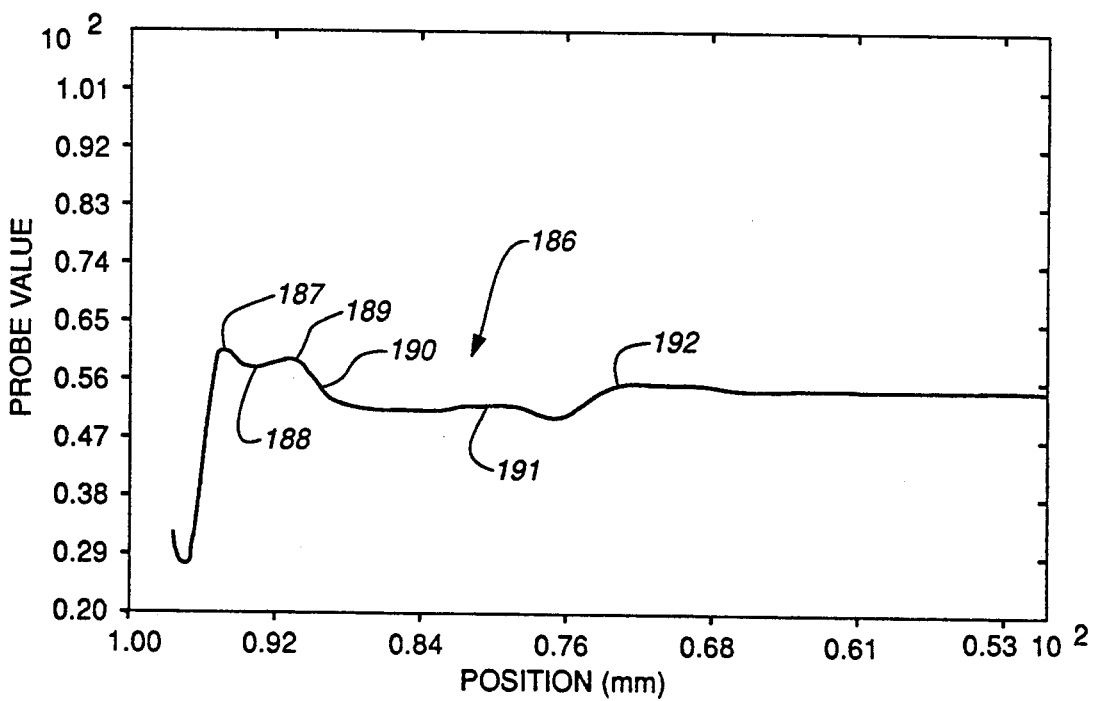
FIG._26

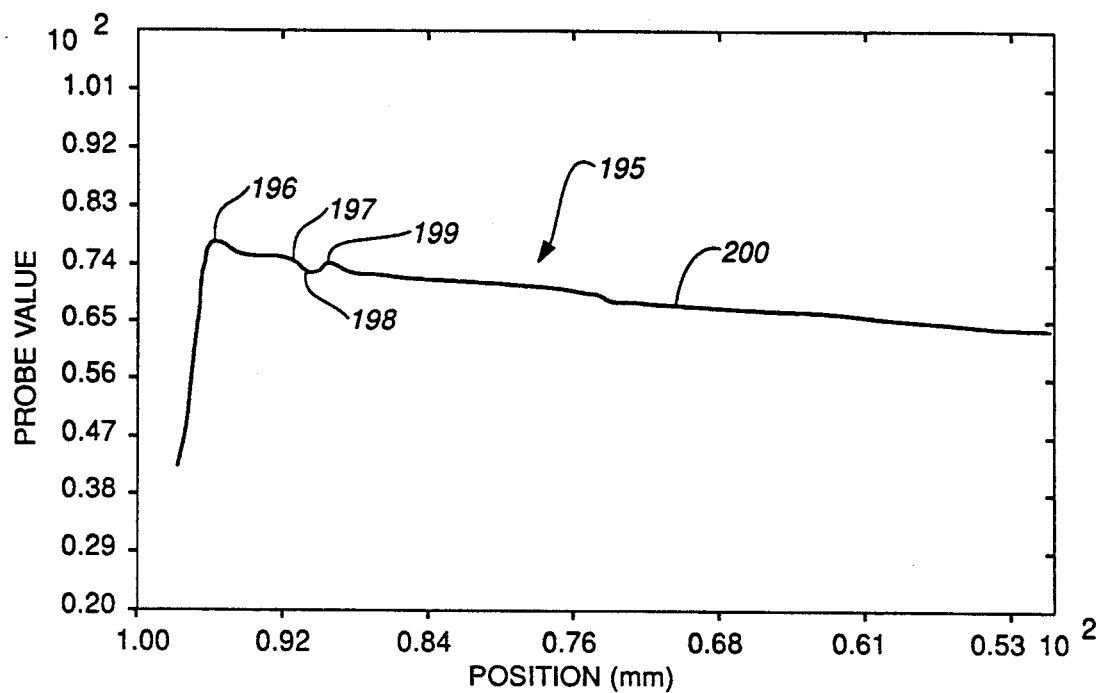
FIG._27
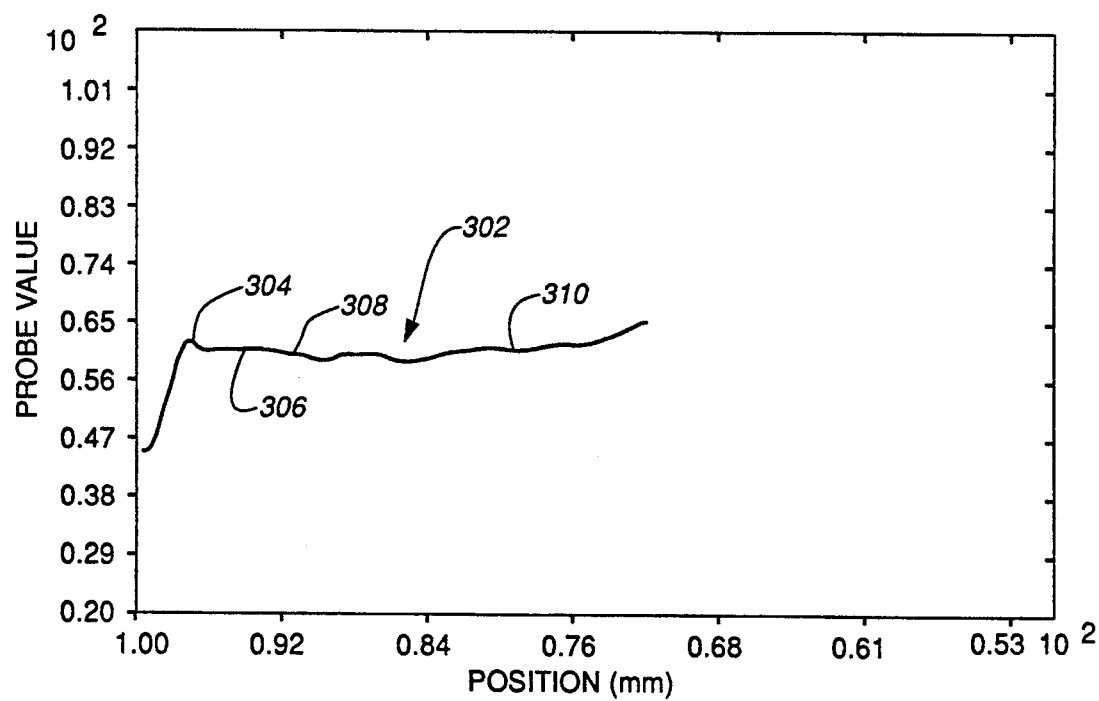
FIG._28

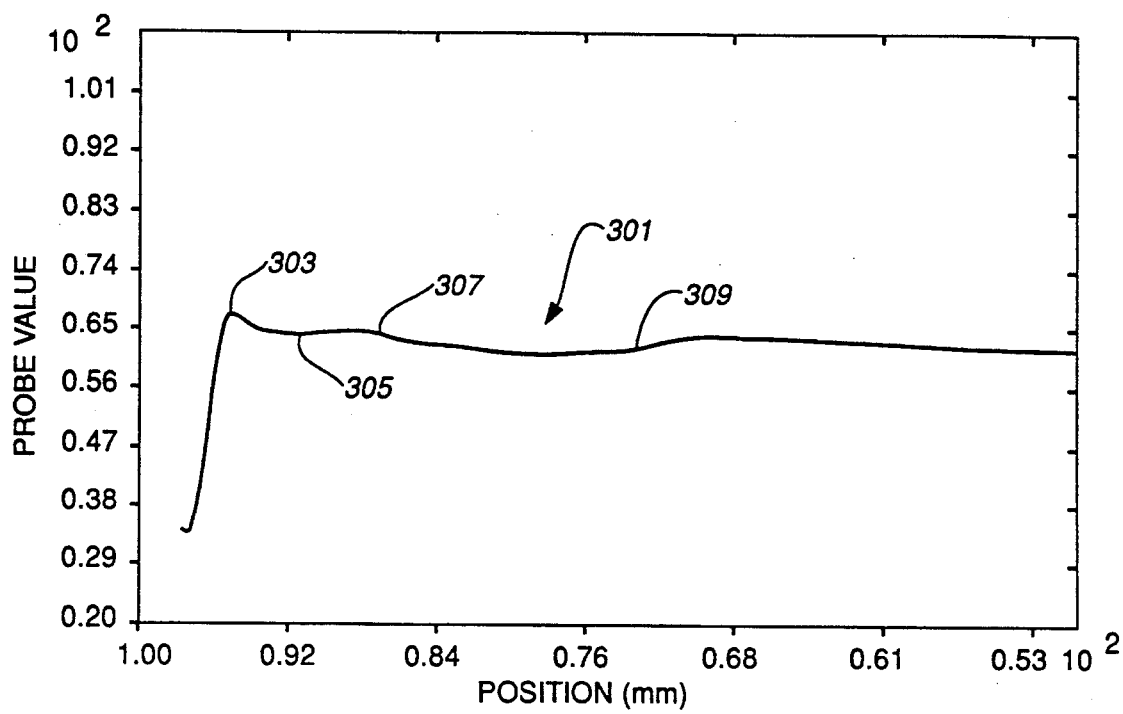
FIG._29
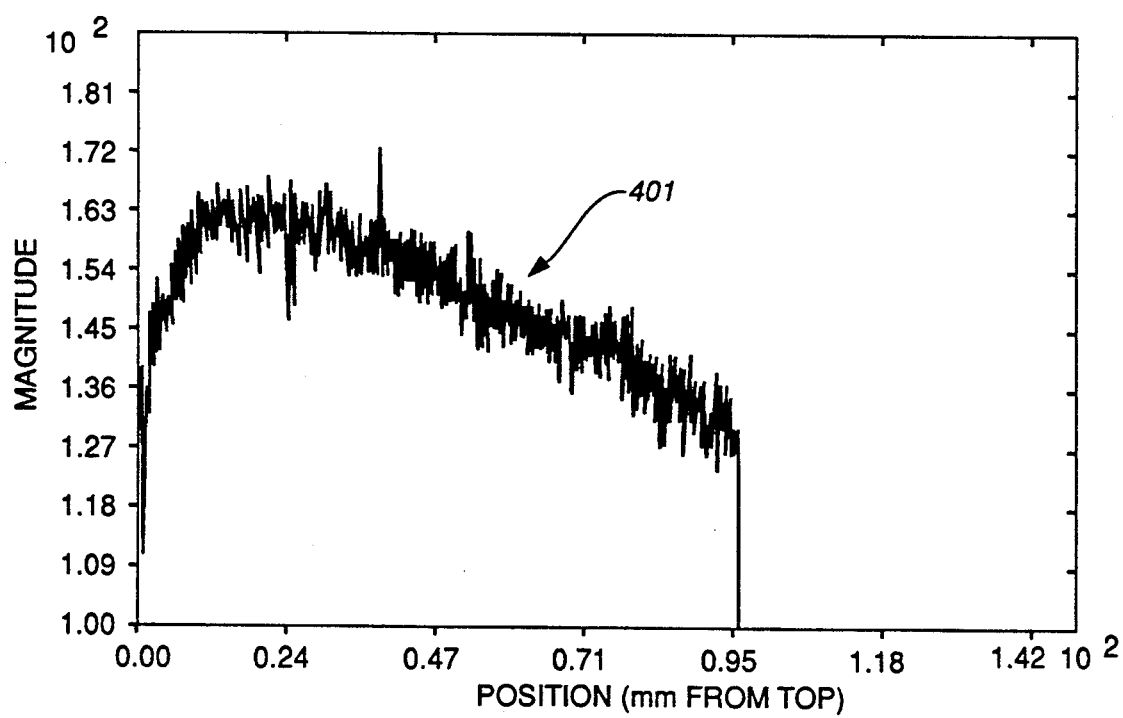
FIG._30

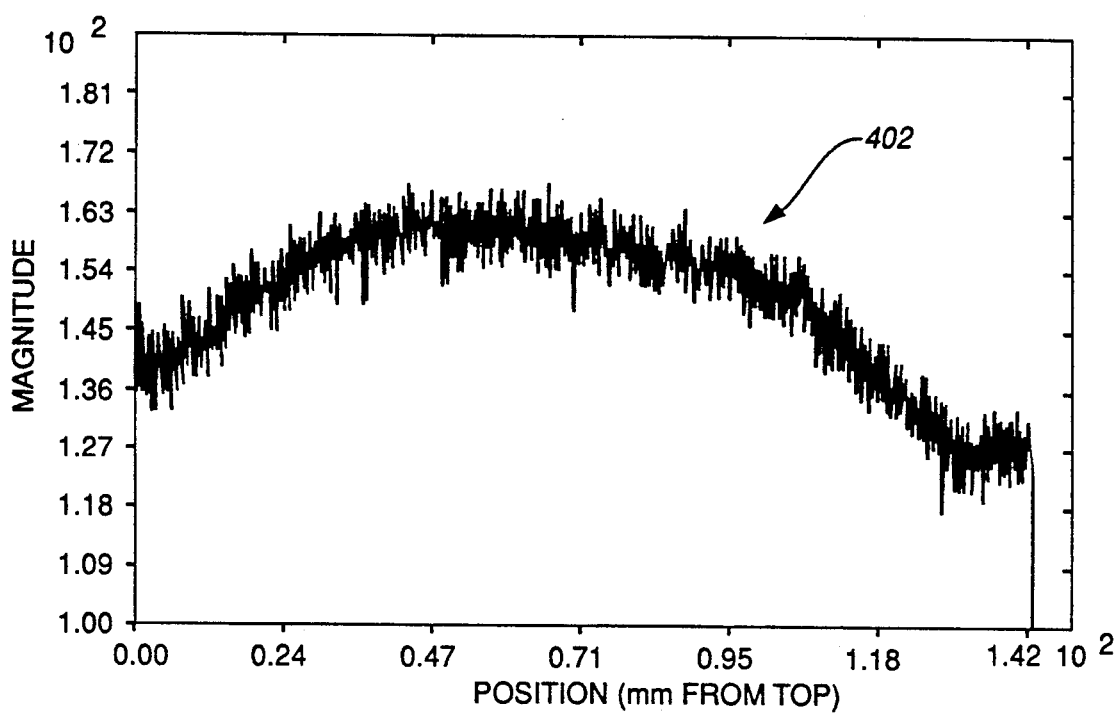
FIG._31

APPARATUS AND METHOD FOR SEDIMENTATION BASED BLOOD ANALYSIS

TECHNICAL FIELD

The present invention relates, in general, to apparatus and methods for the analysis of blood specimens, and more particularly, relates to apparatus and methods for sedimentation-based analysis of blood specimens and the correlation of such analysis with inflammatory conditions.

BACKGROUND ART

Since at least the 1920s, the analysis of blood based upon the sedimentation or separation of erythrocyte cells from blood plasma has been extensively undertaken. Two classic sedimentation techniques are most commonly employed, namely, the Wintrobe method and the Westergren method. These techniques each utilize observation and recording of the settling of erythrocyte or red cells in a blood specimen from the relatively clear white cell-containing plasma fluid. As the red cells settle, a separation boundary between the erythrocyte cells and clear plasma occurs and drops or moves down the tube with continued red cell settling.

During settling, the erythrocyte cells periodically stack in structures known as "rouleaux" and start to gravitate through the fluid plasma toward the bottom of the settling tube. The relative movement between the rouleaux and plasma causes the rouleaux to breakdown and setting to be slowed. This process is repeated with time and affects the rate at which the separation boundary settles. The amount or drop of the separation boundary in a predetermined time interval, for example one hour, has been referred to as the "settling rate" of the blood sample. This settling rate has been found to have a significant, although not very specific, correlation with the presence of inflammatory diseases and/or conditions.

While classic sedimentation rate measurements provide some useful information as to the presence or absence of inflammatory conditions in a patient, they inherently have been incapable of specifically identifying conditions or diseases, and they have not been very useful in tracking the progress of, or degree of involvement in, the disease.

Attempts have been made to gain more useful data from blood specimen settling or sedimentation. Additionally, various apparatus have been employed to attempt to automate the sensing and recording of erythrocyte cell sedimentation. The attempts to automate the classic sedimentation rate measurement techniques have generally proceeded along the same line as the original manual approach, namely, to employ an apparatus which transmits radiation, usually radiation in the visible light range, through the test specimen. Various recording and tracking heads have been employed in which the movement of the head occurs when there is a change from an inability to transmit light through the sample to an ability to transmit light. This change occurs when the separation boundary drops down below the position of the light beam emitting and sensing apparatus. Typical of such blood sedimentation apparatus and methods are the devices shown in U.S. Pat. Nos. 2,725,782, 2,982,170, 3,261,256, 3,288,019, 3,422,443, 3,474,458, 3,604,924, 3,631,513, 3,715,761, 3,844,662, 3,952,579 and 4,118,974.

It has been recognized that a single measurement taken one hour or two hours after the specimen is placed in the settling tube only provides one or two points on the "settling curve". Thus, the goal of automating the recording of sedimentation of erythrocyte cells was in part to develop an entire settling curve in the hope that the curve would provide more useful data that could be correlated to inflammatory conditions.

Study of the sedimentation curves produced by various continuous recording apparatus, however, has revealed that accuracy in the correlation of inflammatory conditions with settling curve shapes has not been possible. Diagnosis of inflammatory conditions using the complete settling curve for erythrocyte cells over a one, or even a two hour, settling period has lacked the reliability necessary for a sound diagnosis.

The suggestion is also found in the prior art that the instantaneous rate of settling, or the derivative of the settling curve (change in height divided by the change in time), may yield data which are more helpful and more easily correlated to permit diagnosis of inflammatory conditions than the settling curve itself. Thus, in U.S. Pat. No. 4,041,502 to Williams et al. and a companion article entitled "An Automatic Sedimentimeter" in *Biorheology* (Vol. 14, pp. 145–149, 1977) Misiaszek, Williams, Stasiw and Cerny, an apparatus and method for discrete recording of both the settling curve and the first derivative or instantaneous settling rate of the settling curve are disclosed.

In the sedimentimeter of the Williams et al. patent, a light-emitting diode is mounted next to a vertical settling tube on a movable tracking head. The LED transmits a light beam through the tube to a photodiode detector positioned on the tracking head on the other side of the specimen. When the photodiode detector cannot detect the beam from the LED, the tracking head is below the separation boundary between the erythrocyte cells and fluid plasma. As the separation boundary drops to a position below the beam from the LED, the photodiode detector detects the beam and thereby senses the passage of the separation boundary beyond the current beam position.

The Williams et al. tracking head is moved down the tube by a stepping motor. The LED emits static or constant radiation which continuously irradiates the photodiode through the tube, and if the photodiode detector senses light from the LED above a predetermined threshold level, the stepping motor is actuated to drop the tracking head. The system includes a clock and logic circuit which operates the stepping motor for a period of time sufficient to cause the amount of light sensed by the photodiode detector to drop below a certain level, at which point the stepping motor ceases operation. A recording circuit samples data as to the time which the motor has operated every 15 seconds and records the length of time of operation of the stepping motor for each 15 second interval to thereby provide a record of the motion of the tracking head and the separation boundary.

In order to obtain further data for correlation with diseases, in the Williams et al. patent the approximate slope of the sedimentation curve or the instantaneous rate of sedimentation also is calculated. This is accomplished by determining the drop in distance of the tracking head for each 15 second interval of time over the entire settling period, usually one hour.

The instantaneous settling rate or first derivative of the settling curve which is produced by the Williams et al. apparatus was thought to produce data that would be more likely to be able to be correlated with inflammatory conditions. For example, the first derivative or slope curve might yield information as to the formation and breakdown of rouleaux, which may be an indication of the presence or absence of an inflammatory condition. Thus far, however, the hoped-for correlation of the settling rate data with inflammatory conditions has not been realized, and erythrocyte cell sedimentation studies still have not been proven to be capable of reliable disease diagnosis.

Other articles in the technical literature since the Williams et al. patent which discuss erythrocyte cell sedimentation and the continuing limited usefulness of sedimentation rates as a diagnostic tool include:

"The Age-Related Hemorheological and Osmotic Properties of Human Blood," by Cerny et al., *Biorheology*, Vol. 74, No. 182, pp. 85-89 (1978);

"The Erythrocyte Sedimentation Rate of Blood Reconsidered," by Merrill et al., *Biorheology*, Vol. 74, No. 182, pp. 90-95 (1978);

"Optical Method for Haematocrit Determination," by Singh et al., *Medical & Biological Engineering & Computing*, Vol. 20, pp. 527-528 (July, 1982);

"The Erythrocyte Sedimentation Rate Time Curve: Critique of an Established Solution," by Dorrington et al., *Biomechanics*, Vol. 16, No. 1, pp. 99-100 (1983); and "Erythrocyte Sedimentation Rate—From Folklore to Facts," by Bedell et al., *The American Journal of Medicine*, Vol. 78, pp. 1001-1009 (June, 1985).

The white cell-containing plasma above the settled erythrocyte cells has largely been ignored as a source of usable sedimentation-based data. In patients having a significant one-hour erythrocyte settling rate, for example, over about 7 millimeters, however, bands or layers of white cells can be seen to occur above the settled red cells. This white cell banding suggests that sedimentation is occurring in connection with the different types of white cells. While various clinical tests have been devised for white cells, they have not previously included attempts to obtain data useful in the diagnosis of inflammatory conditions from white cells based upon their settling and banding characteristics.

Accordingly, it is an object of the present invention to provide a process and apparatus which is capable of a sufficiently accurate determination of the instantaneous settling rate of erythrocyte cells to enable the diagnosis of specific inflammatory conditions.

Another object of the present invention is to provide an erythrocyte sedimentation tracking process and apparatus in which data is sampled when changes in the cell settling rate actually occur, rather than at timed intervals, to enable sensing of the occurrence of changes in sedimentation.

Another object of the present invention is to provide an erythrocyte sedimentation tracking process in which changes in red cell sedimentation which are affected by rouleaux formation and rouleaux breakdown, and protein-protein interaction can be recorded and used to correlate settling with inflammatory conditions.

A further object of the present invention is to provide an erythrocyte sedimentation-based process for diagnosing inflammatory conditions in which changes in settling characteristics of erythrocyte cells as they settle past a sensing zone are determined.

Still another object of the present invention is to provide an erythrocyte sedimentation instrument and process which is more sensitive to changes in settling rates and provides more data for the statistical analysis necessary for correlation to inflammatory conditions.

A further object of the present invention is to provide an instrument and process which senses and samples a characteristic (preferably reflectivity) of settling of fluid plasma containing white cells and enables correlation of a sampled fluid plasma characteristic to inflammatory conditions.

Another object of the present invention is to provide an apparatus and process for the tracking of instantaneous settling rates of erythrocyte cells which is self-calibratable to each test specimen of blood for improved accuracy and higher correlation of instantaneous sedimentation rates with inflammatory conditions.

Still a further object of the present invention is to provide a process for the use of repetitive patterns occurring in one or all of: erythrocyte instantaneous settling rates, white cell reflectivity scans, erythrocyte reflectivity scans, and erythrocyte reflectivity immediately after a settling increment occurs, in the identification of inflammatory conditions.

Another object of the present invention is to provide a blood cell sedimentation apparatus which is relatively simple and inexpensive to construct, operate and maintain.

A further object of the present invention is to provide a cell sedimentation apparatus which is capable of obtaining useful data from both red cell and white cell sedimentation.

Still another object of the present invention is to provide a method for obtaining useful red and white cell sedimentation data which can be automated and produces data suitable for computer analysis and computer correlation to inflammatory conditions.

The apparatus and process of the present invention have other objects and features of advantage which will become apparent from or are set forth in more detail in, the accompanying drawing and the following description of the Best Mode of Carrying Out the Invention.

DISCLOSURE OF INVENTION

The present apparatus for determining settling-based phenomena of both red and white cells in a test specimen of blood includes a settling tube, a sensing assembly mounted proximate the settling tube for sensing a characteristic of the blood cells and/or plasma during settling, a control assembly responsive to the sensing assembly to cause the sensing assembly to be displaced during sensing and sampling, and a data sampling apparatus responsive to at least one of the sensing assembly and the control assembly to sample data indicating settling of the blood cells.

The improvement in one aspect of the present invention is to provide an apparatus and method which yields data as to the settling of erythrocyte cells from white cell-containing fluid plasma, which data can be more accurately correlated with inflammatory conditions. Thus, in the improved apparatus and method the sensing assembly is operated to sense a desired characteristic, preferably reflectivity, at a sensing rate which is high relative to the rate of occurrence of a significant settling of erythrocyte cells, for example about 50 times faster than the red cell settling rate. Moreover, in the improved apparatus and process sensed data is sampled, i.e., stored and used, only upon the occurrence of a significant settling of the erythrocyte cells, for example, upon settling of cells by an amount which will cause the sensed characteristic to cross a predetermined threshold. In this aspect of the invention settling rate curves are generated using data sampling at times which are determined by settling activity, not arbitrary time intervals.

In another aspect, the improvement in the instantaneous erythrocyte settling rate apparatus and method of the present invention is comprised, briefly, of the control assembly being responsive to the sensing assembly to maintain the sensing assembly located in a movable tracking zone during settling, which tracking zone is located from a position proximate and below the separation boundary to a position up to the separation boundary. Thus, sensing and sampling occurs by sensing a change in a characteristic of the test specimen in a tracking zone containing the erythrocyte cells, rather than in the fluid plasma portion of the specimen. Moreover, sensing preferably not only uses changes in a characteristic, such as reflectivity, to track settling, but also includes sensing the absolute value of the characteristic, reflectivity, essentially immediately after a settling event occurs.

In yet another aspect of the present invention the improvement is comprised of sensing and sampling a settling characteristic, such as reflectivity, in a stationary settling zone a spaced distance below the separation boundary while settling of the separation boundary proceeds down to said settling zone.

In still a further aspect of the present invention, the apparatus and method include a fluid plasma scanning assembly movably mounted proximate the settling tube and formed to scan a characteristic, such as reflectivity, of the plasma fluid in a scanning zone above the separation boundary between the erythrocyte cells and the plasma fluid.

In the various aspects of the present invention, static or pulsed irradiation may be used. Radiation in the infrared frequency range is preferred, but for some purposes, for example, white cell typing, radiation in the visible light range may be more advantageous. Usually reflectivity is the sensed and sampled characteristic, but transmissivity of the test specimen also can be used.

BRIEF DESCRIPTION OF THE DRAWING

FIG. 1 is a graphic representation of a portion of an erythrocyte settling curve produced using prior art apparatus and methods.

FIG. 2 is a graphic representation of a tracking head displacement curve corresponding to the settling curve of FIG. 1.

FIG. 3 is a front elevation view of an apparatus for determining the settling characteristics of erythrocyte cells and white cells constructed in accordance with the present invention.

FIG. 4 is a side elevation view of the apparatus of FIG. 3 shown connected to control and computation apparatus.

FIG. 5 is a top plan view of the apparatus shown in FIG. 3, with the cover removed.

FIG. 6 is a graphical representation of a tracking head displacement curve using the apparatus of FIG. 3.

FIG. 7 is an enlarged, fragmentary, side elevation view, in cross-section, of a schematic representation of the settling tube and sensing head of the apparatus of FIG. 3.

FIG. 8 is an enlarged, fragmentary, top plan view, in cross-section, of a schematic representation of the tracking head and settling tube taken substantially along the plane of line 8—8 in FIG. 3.

FIG. 9 is an enlarged, fragmentary, end elevation view of the sensing head of the apparatus of FIG. 3.

FIG. 10 is a schematic representation of a control circuit used to control motion of the sensing head in the apparatus of FIG. 3.

FIG. 11A is a computer display print-out of a settling curve generated using the apparatus of FIG. 3 for a pregnant female in her first trimester.

FIG. 11B is a computer display print-out of an instantaneous erythrocyte settling rate curve based upon the curve of FIG. 11A.

FIG. 11C is a computer display print-out of a Fast Fourier Transform of the settling curve of FIG. 11A.

FIG. 11D is a computer display print-out of a Fast Fourier Transform of the settling curve of FIG. 11A with the first data point omitted.

FIG. 12A is a computer display print-out of a settling curve for another pregnant female in her first trimester.

FIG. 12B is a computer display print-out of an instantaneous settling rate curve corresponding to the curve in FIG. 12A.

FIG. 12C is a computer display print-out of a Fast Fourier Transform of the settling curve of FIG. 12A.

FIG. 12D is a computer display print-out of a Fast Fourier Transform of the settling curve of FIG. 12A with the first data point omitted.

FIG. 13 is a computer display print-out of a settling curve for a pregnant female in her second trimester.

FIG. 14 is a computer display print-out of an instantaneous settling rate curve corresponding to the curve in FIG. 13.

FIG. 15A is a computer display print-out of a settling curve for a pregnant female in her third trimester.

FIG. 15B is a computer display print-out of an instantaneous settling rate curve corresponding to the curve in FIG. 15A.

FIG. 15C is a computer display print-out of a Fast Fourier Transform of the settling curve of FIG. 15A.

FIG. 15D is a computer display print-out of a Fast Fourier Transform of the settling curve of FIG. 15A with the first data point omitted.

FIG. 16A is a computer display print-out of a settling curve for a female with a chronic fatigue condition.

FIG. 16B is a computer display print-out of an instantaneous settling rate curve corresponding to the curve in FIG. 16A.

FIG. 17A is a computer display print-out of a settling curve for a female who has lung cancer.

FIG. 17B is computer display print-out of an instantaneous settling curve corresponding to FIG. 17A.

FIG. 18A is a computer display print-out of a settling curve for a female having breast cancer.

FIG. 18B is a computer display print-out of an instantaneous settling rate curve corresponding to the curve in FIG. 18A.

FIG. 19A is a computer display print-out of a settling curve for a male suspected of having Acquired Immune Deficiency Syndrome (AIDS) and hepatitis.

FIG. 19B is a computer display print-out of an instantaneous settling rate curve corresponding to the curve in FIG. 19A.

FIG. 20A is a computer display print-out of a settling curve for a male having AIDS.

FIG. 20B is a computer display print-out of an instantaneous settling rate curve corresponding to the curve in FIG. 20A.

FIG. 21 is a computer display print-out of a plasma fluid scan for the patient of FIGS. 11A-D.

FIG. 22 is a computer display print-out of a plasma fluid scan for the patient of FIGS. 12A–D.

FIG. 23 is a computer display print-out of a plasma fluid scan for the patient of FIGS. 13 and 14.

FIG. 24 is a computer display print-out of a plasma fluid scan for the patient of FIGS. 15A–D.

FIG. 25 is a computer display print-out of a plasma fluid scan for the patient of FIGS. 16A–B.

FIG. 26 is a computer display print-out of a plasma fluid scan for the patient of FIGS. 17A–B.

FIG. 27 is a computer display print-out of a plasma fluid scan for the patient of FIGS. 18A–B.

FIG. 28 is a computer display print-out of a plasma fluid scan for the patient of FIGS. 19A–B.

FIG. 29 is a computer display print-out of a plasma fluid scan for the patient of FIGS. 20A–B.

FIG. 30 is a computer display print-out of a reflectivity measurement curve for a pregnant patient in her first trimester.

FIG. 31 is a computer display print-out of a reflectivity measurement curve for a female patient with breast cancer.

BEST MODE OF CARRYING OUT THE INVENTION

The blood sedimentation-based diagnosis apparatus and process of the present invention is based in part upon a principle found in the prior art, namely, tracking the separation boundary between erythrocyte cells as they settle from the remaining plasma fluid. Prior separation boundary tracking apparatus and methods, however, have employed techniques which inherently are incapable of generating data that can be reliably correlated to specific diseases and further introduced inaccuracies and noise into the tracking measurements so as to mask the data obtained.

Prior Sedimentimeters—Detail

In FIG. 1, a section of a sedimentation curve 201 is shown which would be generated by the apparatus and method of prior art U.S. Pat. No. 4,041,502 to Williams et al. Actually, curve 201 has had its slope reversed from curve S in FIG. 3 of Williams et al., patent and it has been drawn as straight line segments between a plurality of data points 202–207.

The Williams et al. apparatus and method are based upon the sampling of sensed data at fixed, predetermined time intervals, namely, every 15 seconds. While the Williams et al. LED and photodiode operate or sense continuously, the sampling circuit looks at the total motor displacement (excursions), or samples sensed data, only at fixed time intervals of 15 seconds.

As can be seen in FIG. 2 of the present application, Williams et al. apparatus has a light transmission threshold 209 above which the stepping motor is supposed to operate and below which the motor is shut down. It is believed, however, that if the motor in Williams et al. is turned off at threshold 209, dropping of the boundary between red and white cells permits more light to pass through to the photodiode, which turns the motor back on. There inherently is, therefore, some hysteresis in the servo circuit and stepping motor which effectively results in a second or "motor on threshold" 210.

If a theoretical single threshold 209 truly existed, the stepping motor would be continuously operating since the cells are settling virtually all of the time, but not necessarily at the same rate as the stepping motor operates. The tracking head movement which is most likely to occur using the Williams et al. apparatus, therefore, is believed to be the solid line stepped curve 211 in FIG. 2, which corresponds to the two threshold light transmission curve 212. If one threshold 209 truly were controlling, broken line curve 213 would illustrate the motion of the Williams et al. tracking head. In either case, the straight line segment 214 between data points 202 and 203, which segment forms curve 201 in FIG. 1, does not reflect the actual displacement of the tracking head.

Each of segments 214–218, in Williams et al., therefore, is an approximation of the tracking head motion, which approximation does not reflect the sedimentation which is occurring between the data points taken every 15 seconds. Moreover, and very importantly, the selection or sampling of data in Williams et al. is driven arbitrarily. Data points 202–207 only coincidentally (and rarely) are taken at times when significant settling rate changes are occurring.

As may be seen from FIG. 2 of the present application, the Williams et al. curve segment 214 completely misses the knee and slope reversal present in more accurate curve 213, and for that matter in stepped curve 211.

During a one hour test, the Williams et al. apparatus generates a total of only 240 data points. Obviously, the approximation which is the settling curve generated by the Williams et al. apparatus becomes even less accurate when the first derivative is calculated. The arbitrarily selected data points are used to compute a change in height, $\Delta h$, which is then divided by the change in time, $\Delta t$, during which the height change occurred. In Williams et al., $\Delta t$ is always 15 seconds.

In Williams et al., therefore, the instantaneous settling rate or first derivative curve is, in fact, only a rough approximation or a macro-curve which generally resembles the shape of an accurate slope curve, but clearly is not capable of accurately illustrating the micro-curves (knees and slope reversals) which are actually occurring between data points.

Separation Boundary Tracking

In a first aspect of the present invention, therefore, a much more accurate settling curve and instantaneous settling rate curve are obtained by sensing at a very high rate and sampling sensed data when significant settling occurs.

As used in this application, the expressions "sensing" and "sensed" shall mean the receipt of a signal from the test specimen indicating a characteristic of the specimen, for example, a signal indicating the amount of reflectivity of the specimen to infrared radiation. Thus, the reflectivity level of the specimen may be sensed every 10 milliseconds, but not necessarily sampled or measured. The expressions "sampling" and "sampled" shall mean one or both of: (i) the sensed characteristic is stored, recorded or captured, or (ii) the sensed characteristic is used to store, record or capture related data to the sensed characteristic, such as, the time at which the sensed characteristic exceeded or fell below a threshold level. The expression "measured" shall mean that the absolute value of the sensed characteristic has been stored or recorded. Thus, the amount or sensed quantity of the reflectivity is recorded, as opposed to sampling or recording of related data, such as the time.

In the sedimentation sensing apparatus and process of the present invention data sampling or capture is driven by significant settling of the erythrocyte cells, regardless of the timing of such settling, while in the prior art data sampling or capture was driven by time, regardless of the settling activity. Settling-driven data capture is achieved in the present invention by sensing data at a rate which is much higher than the occurrence of significant red cell settling, and sampling in response to the sensed characteristic when significant settling occurs. This approach allows the present apparatus and method to capture the micro-curve data which has not previously been available for use in correlating curve patterns with inflammatory conditions.

Other, probably second order, problems are present in prior art systems such as Williams et al., which employ the transmission of light through the test specimen in order to effect tracking. Such instruments are operating constantly above the separation boundary or meniscus between the settling erythrocyte cells and the plasma fluid, because the motor on threshold requires transmission of light through the specimen above the separation boundary. Data taken in this area, however, is subject to significant masking phenomena.

The formation and breakdown of rouleaux, with associate relative upward migration of plasma and white cells, can produce miro-turbulence at the separation boundary in which red cells are carried temporarily up into the plasma. These red cells reduce the transmissivity of the specimen above the separation boundary. Additionally, the separation boundary tends to have an upwardly concave meniscus. Thus, transmissivity can be influenced by the surface tension or the meniscus at the separation boundary.

Still further, the white cells immediately above the separation boundary also are settling, and light or radiation transmission through the plasma fluid containing white cells at and above the separation boundary can vary, not as a function of erythrocyte cell settling, but as a function of settling of the white cells contained in the plasma fluid.

The combined masking effect probably is not significant in the Williams et al. apparatus and method because the long sampling interval has an even greater masking effect. However, when more accurate tracking is undertaken, the use of a method based upon transmission of radiation through the specimen above the separation boundary is believed to be inherently less accurate than sensing a characteristic below the separation boundary.

In the sedimentation apparatus and process of the present invention tracking of the separation boundary movement is achieved most preferably by sensing the reflectivity of the erythrocyte cells, and in the preferred form, the reflectivity to a static beam of infrared radiation is sensed. Thus, by employing an infrared beam, which is reflected against the settling erythrocyte cells proximate and below the separation boundary, an increase in reflectivity resulting from settling of red cells just prior to and at the separation boundary is used to control movement of the present tracking head. This process, therefore, can proceed without the tracking head ever "seeing" the plasma fluid-containing white cells or reaching the upwardly concaved meniscus of the erythrocyte cells on the walls of the settling tube.

The sedimentation instrument and process of the present invention can be described in further detail by reference to FIGS. 3, 4 and 5. A blood cell settling measurement instrument, generally designated 21, is provided for determining the settling of both red and white cells in a test specimen of blood. Mounted in measuring instrument 21 is a standard blood settling tube, 22, which is preferably a Wintrobe blood settling tube (such as a model 6901 SEDITUBE having a 3.15 millimeter internal diameter). It will be understood, however, that a Becton-Dickinson VACUTAINER settling tube, Westergren settling tube or other settling tube also could be used in the present apparatus and process. Tube 22 is slidably received in collar 23 and a socket 24 in the instrument framework or support stand. Securement means, such as a spring-biased detect assembly, or even a thumbscrew 26, secures the specimen tube firmly in place in the instrument.

A blood specimen is prepared in a standard manner, corresponding to the type of blood settling tube 22 employed in the instrument. The preparation of the test specimen will not be described herein and does not constitute a novel portion of the present invention. It is contemplated, however, that the apparatus and process of the present invention can be used with blood specimens to which non-standard additives have been added. For example, additives which accelerate red cell settling can be used for both red cell studies and white cell studies.

Mounted proximate settling tube 22 is a sensing means, generally designated 31, which is formed to sense a characteristic of the test specimen of blood during settling. In prior art apparatus, the sensing means sensed the transmissivity of the test specimen during settling. Sensing means 31 of the present invention preferably is formed to sense the reflectivity of the specimen in an attempt to enhance further the accuracy of the data gathered. As above set forth, it is believed that radiation transmission through the specimen produces less accurate data. It will be understood, however, that settling-driven data capture or sampling also would yield significantly enhanced settling and instantaneous settling rate data, as compared to prior art instruments, even if the present instrument employed transmissivity through the specimen instead of reflectivity off the specimen. In the broadest aspect of the invention, therefore, the characteristic sensed can be transmissivity, reflectivity, or another characteristic which changes during settling of the erythrocyte cells, as long as data capture is driven by settling and the sensing rate is sufficiently high relative to the settling rate to insure sampling when significant settling occurs.

Sensing means 31 is most preferably mounted to a movable sensing or tracking head 42 and movement of tracking head 42 is, in turn, controlled by control means that is responsive to signals from the sensing means. The control means causes the tracking head to follow the separation boundary between erythrocyte cells and plasma fluid during settling of the red cells in the settling tube. Control means of the present invention preferably includes a stepping motor 32 which is coupled electrically by conductor means 33 to a control circuit 34 coupled to computer processing unit (CPU) 36 (FIG. 4). Signals from sensing means 31 are transmitted by conductor means 37 to control circuit 34 and from the control circuit to CPU 36 in a manner described more fully hereinafter.

Stepping motor 32 drives a drive pinion 39 which is matingly engaged with a rack 41 that is movably mounted to linear bearing 40. Raising and lowering of tracking head 42 is the result of displacement of rack 41 on which the sensing means 31 is mounted (for example, by retainer member 43). The storing or recording of the settling data and the approximate instantaneous settling rate data is accomplished by CPU 36, which acts as sampling means responsive to at least one of the sensing means and control means to sample and store data and calculate the approximate instantaneous settling rate.

It should be noted that in the present invention the approximate instantaneous settling rate which is calculated is not strictly the first derivative of the settling curve. Instead, the present apparatus and method calculate a "divided difference," which is equal to a change in height of the separation boundary divided by the time difference or interval in which the change in height occurs. As will be set forth in more detail below, the change in height is a constant, k, in the preferred embodiment of the present invention, and the time difference, or the time interval during which the constant height change occurs, is a variable. Thus, the approximate instantaneous settling rate is a divided difference curve, namely, $\Delta h/(t_2-t_1)$ or $k/\Delta t$.

In the improved cell settling instrument of the present invention, sensing means 31 and control circuit 34 are formed to sense a settling characteristic, such as reflectivity, at a very high rate and to sample and/or record that characteristic or the time data when significant settling occurs.

Computer 36, through control circuit 34, senses the level or reflectivity output of sensing means 31. As erythrocyte cells settle, the reflectivity of the specimen proximate and below the separation boundary between plasma containing white cells and the red cells starts to increase, i.e., there are fewer red cells to absorb the infrared beam and proportionately more white cells and plasma, and thus, more of the beam is reflected. As the reflectivity of the specimen increases to a predetermined threshold, for example, between about 5 percent and about 20 percent above a calibrated reflectivity level of the specimen, the CPU, through control circuit 34, actuates stepping motor 32 and tracking head 42 is lowered which, in turn, lowers the sensed reflectivity. At the same time, the CPU stores or samples the time at which the reflectivity exceeded the predetermined threshold and the position data of the tracking head similarly is correlated to the time data which has been sampled.

The operation of stepping motor 32 and control circuit 34 to achieve settling-driven data capture can best be understood by reference to FIG. 6. In FIG. 6, data points 202 and 203, as well as connecting curve segment 214 from FIG. 2 for the prior art Williams et al. apparatus are shown. In the reflectivity-based system of the present invention stepping motor 32 is actuated for one step any time the reflectivity rises to a "Motor On Threshold" level 220. Data point 202 occurs when a step of the stepping motor is completed and the reflectivity sensed by sensing means 31 is at point 221 below threshold 220.

As the erythrocyte cells settle, the decreasing density of the erythrocyte cell proximate the approaching separation boundary 48 results in an increasing sensed reflectivity until point 222 is reached at the threshold level 220. When level 220 is reached, CPU 36 steps motor 32 by one step, which reduces the sensed reflectivity again to a level 230 below threshold 220. This process is repeated over and over during the full settling period.

At each step taken by the stepping motor, the time at which the step occurred is stored or captured in CPU 36 and provides a data point for the settling and divided difference curves of the present invention. Thus, in FIG. 6, there are 10 data points between data points 202 and 203, and the micro-curve 213 can be drawn between these points to much more accurately track the erythrocyte settling than the simplistic curve segment 214.

In the present invention, therefore, the data sampling means 36 is responsive to a change in a sensed settling characteristic, not an arbitrary time interval, to capture, sample or record data. The settling characteristic sensed by sensing means 31 is reflectivity of the specimen and this characteristic changes with specimen settling.

If the rate of sensing the settling characteristic is high relative to the occurrence of a measurable or significant amount of settling, the data sampled will be relatively accurate. It is not currently known precisely how much faster the sensing rate should be than the measurable settling rate to produce data that is sufficiently accurate to enable the correlation of settling to inflammatory conditions, but sensing at a rate of about 50 times the maximum expected settling rate for erythrocyte cells appears to produce data which is sufficiently accurate for correlation. It may be, however, that a sensing rate of ten times or only three times faster would suffice, particularly as the size of the steps is decreased.

In the apparatus of the present invention reflectivity sensing rates have been employed in the range of once every 0.01 to 0.002 seconds. In FIG. 6 vertical lines 223 represent such sensing times, and it will be seen that reflectivity is increasing from point 230 toward level 222 at each sensing time 223.

Stepping motor 32 in the illustrated apparatus steps sensing means 31 down by 0.034036 millimeters for each step. Using the present invention, maximum settling rates of erythrocyte cells high enough to produce stepping of motor 32 twice in one second have been observed. The maximum rate of erythrocyte cell settling, therefore, may be about one 0.034036 millimeter step every 0.5 seconds, or about 0.068 millimeters per second.

A sensing rate of once every 0.01 seconds, therefore, is 50 times faster than a settling step would occur under maximum settling conditions, and a sensing rate of once per 0.002 seconds is 250 times faster than settling sufficient to cause the motor to take a step.

The sensing rate, therefore, should be sufficiently high, relative to the maximum expected settling rate, that the sensed settling characteristic will be sampled at essentially the same relative time during settling. Thus, time data will be sampled or stored each time the reflectivity reaches level 220 plus or minus 0.01 seconds, which will give a high degree of confidence that separation boundary is in the same position relative to sensor 31 for each time a step is taken.

Using the example of FIG. 6, the method and apparatus of the present invention would generate 12 data points in 15 seconds and a 0.41 millimeter drop of separation boundary 48, while the apparatus of the Williams et al. patent would generate two data points. Moreover, the data points using the present apparatus increase in number during periods of rapid settling and are captured when settling occurs, not at predetermined time intervals.

The divided difference curve generated using the present apparatus is based upon $\Delta h/(t_2-t_1)$. While $\Delta h = k = 0.034036$ millimeters, $\Delta t_1$ is not normally equal to $\Delta t_2$ and may vary substantially. The divided difference, or approximate instantaneous settling rate, data based upon micro-curve 214, therefore, also is much more accurate. In FIG. 6, for example, the slope of curve 214 is 0.41/15=0.0273 mm/sec. By contrast, the slope of curve 213 at segment 228 is 0.034036/0.75=0.0454 mm/sec.

In addition in the improved sedimentation tracking instrument of the present invention, sampling means 36 is responsive to sensing means 31 to maintain the sensing means located in a movable tracking zone which is centered proximate and below separation boundary 48 up to a position at, but not above, the separation boundary. The sensing means in the present invention is sensing a change in the characteristic of the test specimen in a tracking zone which includes the settling erythrocyte cells, rather than operating in the plasma above the erythrocyte cells.

Tracking Head

As best may be seen in FIG. 7, blood specimen 46 is placed in settling tube 22. Initially the specimen is a mixture of erythrocyte cells, white cells and fluid plasma which is substantially uniform and unsettled and extends to level 47 in the settling tube. As settling begins, a separation boundary 48 between the settling erythrocyte cells 49 and the relatively, but not completely, clear plasma fluid 51 begins to occur. As the separation boundary sinks or drops down tube 22, the control circuit and CPU in the instrument of the present invention position sensing means 31 in a tracking zone, Z, which extends from a position 52 below separation boundary 48 to a position 53.

In FIG. 8, a beam or band of static radiation 56 can be seen to be transmitted from transmitter means 57 through tube wall 22 until it meets specimen 46 in tracking zone Z. The beam then is reflected from specimen 46 as reflected beam 58. A portion of reflected beam 58 passes out of tube 22 to reflectivity detector means 59. Part of beam 56 is reflected at surface 50 of specimen 46 and part is absorbed and/or reflected out of the specimen inwardly of surface 50. Control circuit 34 and CPU 36 sense the amount or the intensity of the reflected beam and determines whether or not to lower rack 41 and tracking head 42. In the preferred form, angle $\alpha$ of transmitter 57 from a plane 60 through the center of the tube is equal to about 20°, although it may conveniently fall in the range of about 10° to about 40°, and angle $\beta$ of receiver/sensor 59 is about equal to the angle $\alpha$ on the other side of plane 60.

As illustrated in the drawing, radiation 56 is a static beam of infrared radiation. It is believed that radiation pulses can be used to increase the sensitivity of the present instrument even further. In a pulsed radiation system narrow band peak-to-peak measurements of the reflectivity are sensed by a synchronous detector. This approach also may make simultaneous tracking and scanning possible using multiple sensing heads and pulses of different frequencies so that spurious signals or noise from the other transmitter can be filtered out.

The operation of control circuit 34 and CPU 36, therefore, is to position the reflectivity transmitter/sensor assembly 31 at the tracking zone (FIG. 7). As sedimentation occurs, sensor 31 monitors the reflectivity of the mixture of plasma fluid and erythrocyte cells in the tracking zone. During this process separation boundary 48 drops to the dotted line position in FIG. 7. At or about the time separation boundary 48 reaches beam level 52, the reflectivity of the test specimen will increase by reason of a significantly decreased density of erythrocyte cells. This reflectivity increase occurs even though there are erythrocyte cells above the sensor. The control circuit and CPU, detecting an increase in reflectivity from sensor 31 above predetermined threshold 220 (FIG. 6) actuates motor 32 to step tracking head 42 down by one step to level 52a, which moves the tracking zone Z down to a new tracking zone, Za. While exaggerated in FIG. 7 for the purpose of illustration, tracking zone Z in the preferred form has a height equal to the height of the emitter slit opening 104 as defined by masking 120 (FIG. 9). In the embodiment of the drawing opening 104 has a height dimension of about 1 millimeter. Thus, one step by motor 32 moves tracking zone Z down by 0.034036 millimeters, which is only about 1/30 of the height of the tracking zone Z. This stepping process is repeated over the entire settling period, and enables the apparatus to generate a settling curve and enables CPU 36 to calculate the approximate instantaneous settling rate or the divided difference curve.

Control Circuit

One form of control circuit 34 which is suitable for use with the apparatus and process of the present invention is shown in FIG. 10. Infrared red cell sedimentation sensor 31 and a white cell scanning sensor 81 (the use of which is described below) can be seen to be coupled through amplifiers 91 to analog-to-digital converters 92a and 92b. Converters 92a and 92b transform the analog reflectivity signal received by infrared photodetectors 93 and 94 into 8-bit signals that are transmitted to buffer 96 and subsequently to CPU 36.

The selection as between sensor 31 and sensor 81 is controlled by signals from CPU 36 through address decoder 98, which in turn is coupled through flip-flop 97 to the analog-to-digital converters so as to permit passage of one of the signals to buffer 96. As will be understood, a circuit also could be provided for simultaneous transmission and recording of data from both detectors 93 and 94. As above noted, however, simultaneous transmission by two transmitters probably will require pulsed signals at sufficiently differing frequencies that detectors 93 and 94 do not mistakenly detect spurious signals from the wrong emitter. Similarly, CPU 36 communicates with address decoder 98 to drive flip-flop 99 so that a selected one of infrared emitter 101, for red cell settling sensing, and the white cell scanning infrared emitter 102 is actuated. The flip-flop 97 activates the analog-to-digital converter 92 which corresponds to the actuated one of emitters 101 and 102. When the reflectivity increases by a predetermined amount (e.g., 18%) above a calibrated level stored in the CPU for each tracking position, as set forth below, the CPU further signals the address decoder 98 to actuate motor controller 103 for operation of one of motor drives 104 and 106, which steps one of the stepper motors 32 and 86 by a single step.

The infrared emitters and detectors used in implementing the process and apparatus of the present invention can be an infrared LED and a photo transistor, as for example, are manufactured by Vactec, Model No. VTR17D1, or a pin photodiode can be substituted for the photo transistor. As can be seen in FIGS. 8 and 9, the emitters and detectors preferably are mounted in a housing having a mask 120 defining a slit-opening or window 104 which insures that a relatively narrow band of radiation, e.g., 1 millimeter (0.04 inches) in height and 4 millimeters (0.16 inches) in length, is directed against the test sample. Similarly, the detector preferably has a similarly formed narrow window 106, which reduces the likelihood of detecting spurious signals. The entire instrument is covered by a housing 105 which can be placed over and removed from instrument 21, and which has a black interior surface to reduce ambient signals sensed by detectors 93 and 94.

In order to provide sufficient sensitivity to small steps, analog-to-digital converters 92a and 92b, which normally operate with a five volt window, are voltage controlled to operate with a one volt window. Thus, receiver 93 would normally produce a digital count of 255 from converters 92a and 92b as the voltage from receiver 93 varies from zero to five 10 volts. In circuit 34, converters 92a and 92b have been scaled to have a zero count at about 2.5 volts and a 255 count at 3.5 volts. Thus, each count of output from the converters 92 corresponds to a change in passed voltage of about 3.9 millivolts. Without voltage control of converters 92a and 92b each change in output count would require about a 19.6 millivolt change in input. In instrument 21 a 0.034036 millimeter change produced only a 3 or 4 count maximum change when a full five volt window is used, but changes by about 15 to about 100 counts, depending on the color of the specimen, when a one volt window is used.

Calibration

The effect of using a very sensitive analog-to-digital converter window is that changes induced by settling tube irregularities and differences of color from blood specimen to specimen can introduce significant noise into the data. In order to set the stepping motor threshold 220, and thereby produce uniform and repetitive actuation or stepping of the tracking head for various specimens, it is an important feature of the present invention that the reflectivity for each test specimen of blood and the settling tube be calibrated. The reflectivity of blood varies considerably from patient to patient, making it essential that a means for calibration of instrument 21 be provided.

Calibration of the reflectivity of red analog-to-digital converter 92a for color is accomplished through the following process. Control circuit 34 steps the reflectivity sensor assembly 31 up from a position proximate collar 23 one step at a time while sensing the reflectivity of the combined tube and specimen.

As will be seen in FIG. 10, receiver 93 is connected to differential amplifier 91a, which in turn has digital-to-analog converter 126a connected thereto and driven by CPU 36. At each step up tube 22 from collar 23, CPU 36 varies the offset calibration voltage of converter 126a so as to produce a constant or set output voltage, $V_{set}$, in FIG. 6. In the preferred form $V_{set}$ is equal to 2,696 volts, which is equivalent to a count of 50 on converter 92a. Thus, at the various steps over the scanned height of tube 22, CPU 36 adjusts the offset calibration voltage to produce a constant output voltage to the converter 92a and the digital input required at each position along the tube to produce the constant voltage is stored in memory in the CPU. SINCE CPU 36 is coupled to the stepping motor assembly, the CPU always knows the position of the sensing heads and can use that position information to select from memory the correct input to converter 126a. This calibration removes any differences in reflectivity along the tube due to tube irregularities and also removes variations in reflectivity and changes of color from specimen to specimen.

Voltage threshold 220 (FIG. 6) is set at a level which is sufficiently above $V_{set}$ to insure that the sensed changes in reflectivity are due to settling and not other phenomenon, such a slight color change during aging. Empirically elevating threshold 220 to be between about 5 to about 20 percent above $V_{set}$ seems to provide a threshold above the calibrated reflectivity voltage which causes reflectivity changes to indicate settling.

The voltage threshold 220, for example, may be set to which is 18 percent above $V_{set}$. Thus, the converter 92a generally will be operating at a count level of 200 and below.

Starting the Test

Once the reflectivity calibration for the full height of the tube is stored in CPU 36, the threshold level 220 can be used to locate the top of the specimen and to start the test. Tracking head 42 can be raised until the sensed reflectivity exceeds level 220, which indicates that top 47 of the specimen has been reached.

Circuit 34 then drops the tracking head down by a small amount, for example, 2.5 mm, and begins to sense and store reflectivity of the test specimen at a fixed location. Sensor assembly 31 is maintained at 2.5 mm below the beginning separation boundary height, and the settling test begins when reflectivity increases over threshold 220, or when 3 minutes have elapsed, whichever is earlier. The tracking head then tracks or follows the separation boundary down tube 22, and the time of each change in position of sensor 31 is stored in a data file in CPU 36.

While radiation in the visible light frequency range is believed to be suitable for reflectivity tracking of boundary 48, the preferred form of the apparatus and process employs infrared radiation. It is believed additionally that the process of the present invention also could be performed using photo-optic or fiber optic or laser-driven arrays of sensors to sense at a sufficiently high rate to give enough discrete values of reflectivity in each zone of the settling tube for the settling period (e.g., one hour) to enable correlation with specific inflammatory conditions. It is believed that use of a fiber optic array may enable approximation of a full-height real-time analysis of the entire settling tube.

Utilization of Data

Since the instrument and process of the present invention produce settling curves and divided difference curves which are much more accurate than previously was possible, it is believed that pattern analysis techniques will enable correlation of patterns with specific inflammatory conditions. More particularly, it is believed that a computer implemented neural network will be able to compare sensed specimens with stored "learned" data to match specimen pattern characteristics with known pattern envelopes for inflammatory conditions. Limited clinical testing to date indicates a strong likelihood that distinctive patterns exist.

As will be seen from the Examples below, patterns in divided difference data, or the approximate instantaneous settling rate, seem to reoccur. Additionally, Fast Fourier Transforms of the settling curve data also yield frequency distribution patterns of the frequencies which make up the settling curve that appear to be reoccurring.

The apparatus of the present invention, in fact, resulted in new clinical testing of a patient who originally had not been diagnosed as having Acquired Immune Deficiency Syndrome (AIDS). The patient's divided difference curves strongly suggested the possibility of AIDS, and new clinical evaluation confirmed the presence of the disease.

As also may be seen on the Fourier Transform displays, the word "LOWS" appears, followed by a number. The number indicates the number of times the frequency distribution curve reaches a low point or minimum. Preliminary statistical analysis indicates that the LOWS number can be used with the number of data points taken to produce a Pathology Index which is a better indicator than the ESR as to the degree of sickness of the patient. If the LOWS number is divided by the number of data points, and the result is multiplied by 100 and subtracted from 100, an index number results in the range of 0 to 100 in which patients at the high end of the index are very sick.

Time-Driven Sampling Approximation

Once accurate settling curves have been obtained, it becomes apparent that a measurable drop, i.e., one step, in separation boundary 48 occurs about once every one-half second during rapid settling periods. Accordingly, an approximation of the settling curve can be obtained by time-driven sampling.

If small steps are taken and data is sampled at least twice per second, the resulting settling curve will begin to approximate a sensing driven sampling curve. Thus, for 0.1 millimeter steps, or less, and 0.5 second sampling rates, or higher, the resultant data begins to approximate the more accurate sensing-driven data. If the steps are 0.068 millimeters (twice the preferred step size) and the sampling is taken every 0.05 seconds (10 times the fastest expected settling for one step), a good approximation may result, but it will have two significant disadvantages. First, it is still an approximation. Second, it requires the storing of much more data.

Scanning Erythrocyte at Fixed Locations

In addition to tracking separation boundary 48, it has been discovered that by sensing reflectivity at a fixed location a significant distance below the separation boundary a substantial decrease and then increase in the reflectivity can be measured. This dip in the absolute or measured value of reflectivity is observed at the start of separation boundary tracking.

As above described, sensing head 31 is positioned at 2.5 millimeters below top 47 of the specimen at the start of tracking. If the absolute value of reflectivity is sampled at that fixed location, for example, at about 0.5 second intervals, or faster, a decrease in reflectivity, followed by an increase in reflectivity, is measured.

It is hypothesized that this phenomenon also may be useful in correlation with inflammatory conditions. Thus, there may be a moving band of denser erythrocyte cells and/or rouleaux which precedes boundary 48 and settles down tube 22. By sensing and sampling at a fixed location a significant distance below the separation boundary the passage and characteristics of that moving, more absorbent, band of cells can be determined.

By way of an example, in a two sensing-head system, such as is provided by sensing head 31 and sensing head 81, tracking sensor 31 can be used to sample or measure reflectivity for a first 2.5 millimeter step below top 47, and second head 81, operating at a different frequency and using pulsed infrared radiation to avoid feedback to sensor 31, can be stepped to a position 5.0 millimeters below top 47. Once the separation boundary reaches first head 31, it will track the separation boundary as above described. When boundary 48 reaches second head 81, it will be repositioned by CPU 36 by stepping it down by a significant distance, such as 2.5 millimeters. At the new fixed location head 81 will again sample sensed reflectivity changes to look for the moving radiation-absorbent band of erythrocyte cells.

This process will produce reflectivity measurements showing a series of dips or depressed reflectivity patterns which should provide additional useful data as to blood settling.

At the present time the optimum increment below separation boundary 48 which will reveal the reflectivity dip phenomenon is not known. It is observable at steps of 2.5 millimeters, but a somewhat smaller increment may be acceptable. As used herein, however, the expression a "significant distance" shall mean a distance greater than the height of the sensor beam or pulse (which is currently about 1 millimeter).

It is also possible, although such phenomena have not been studied, that other bands of reflectivity changes could exist at still lower levels below boundary 48. Broadly, therefore, it is a feature of the present invention to scan the erythrocyte-containing portion of the specimen from a fixed location a significant distance below boundary 48 at a high sensing rate and to sample reflectivity data, or time data, as settling occurs to attempt to measure or identify characteristic erythrocyte settling phenomena in the blood specimen below separation boundary 48.

It should be noted that as an alternative to measuring sensed reflectivity, such moving bands of cells also can be identified by time data taken when the reflectivity starts to dip or decrease below a threshold, in a manner similar to tracking head 31 for tracking of the separation boundary. Moreover, multiple thresholds can be used to capture time and/or reflectivity data during passage of the band in front of sensor 81.

Reflectivity Measurement

As above described, changes in reflectivity resulting from erythrocyte settling are used to track the rate of descent of the separation boundary by capturing time data. It is an additional important feature of the present invention that a pattern of measured or absolute values of reflectivity be employed to correlate with inflammatory conditions.

In this process, reflectivity measurement is taken at the same relative time to the settling of red cells, most preferably immediately after a motor step is taken. The high sensing rate above described causes the stepping head to be moved whenever the reflectivity exceeds threshold 220. As can be seen from FIG. 6, however, the drop or decrease in reflectivity which occurs as a result of a single step can vary significantly. Thus, the low points 230 can be seen to represent different levels of reflectivity which result when a single step of 0.034036 millimeters is taken.

In the process and apparatus of the present invention, therefore, the first reflectivity measurement made after stepping the stepping motor (15 milliseconds) also is stored in CPU 36, and a pattern of reflectivity measurements, as a function of the vertical position of the tracking head during settling, can be generated. Since the decrease in reflectivity resulting from a fixed downward step also provides information as to the rate at which erythrocyte cells are settling, the reflectivity measurement pattern also is believed to be susceptible to correlation to inflammatory conditions.

Plasma Scanning

Another aspect of the process and apparatus of the present invention is that the white cells containing plasma above the settled erythrocyte cells can be scanned to produce data which is also useful in diagnosis of inflammatory conditions. More particularly, the apparatus and process of the present invention include means for scanning plasma fluid 51 to sense a characteristic of the plasma fluid which provides data that can be used alone or together with other erythrocyte settling data.

As set forth above, settling instrument 21 preferably includes a second sensing means 81 mounted on a second tracking frame 82. Mounted to linear bearing 85 for vertical reciprocation is rack 83, and a pinion 84 is matingly engaged with the rack and driven by a second stepping motor 86 (FIG. 5). Sensor 81 also preferably is an infrared sensing assembly having a transmitter and an infrared detector/receiver constructed as described in connection with sensing means 31. Sensor assembly 81 can be secured to scanning head 82 by retainer washer 87. Both sensor 81 and stepping motor 86 are coupled to control circuit 34 and CPU 36 by electrical connector cable means for communication of control signals and sensing signals therebetween.

Instead of stepping down with the separation boundary 48, however, sensor 81 is not employed until after a significant amount of settling of erythrocyte cells has occurred. Most preferably, sensor 81 is employed after the one hour settling period, during which sedimentation rates are recorded using sensor 31. It is possible for sensor 31 to be used to perform both the sedimentation tracking and the plasma fluid scanning, if these functions are done sequentially, but having two sensor heads allows overlap in the sensing functions, if needed or desired, as long as feedback is prevented by frequency discrimination or a similar technique. It also is possible to drive sensors 31 and 81 by a single motor if plasma scanning is done after separation boundary tracking. The use of two sensors has the advantage of allowing calibration of red cell sensor 31 to be very precise, while the calibration of white cell sensor 81 can be less precise. It is also possible, however, to use a single sensor 31 and have CPU 36 recalibrate sensor 31 for plasma scanning after erythrocyte tracking is completed.

In the preferred process, once the erythrocyte sedimentation tracking and erythrocyte reflectivity measuring has been completed, control circuit 34 will cause scanning of plasma 51. Plasma scanning will be undertaken only if the one hour erythrocyte settling rate (height drop) is over a predetermined minimum level. Circuit 34 brings scanning head 82 up to the top 47 of specimen 46. Control circuit 34 will thereafter step tracking head 82 and sensor 81 down toward separation boundary 48 of the specimen. At each step, again preferably 0.034036 millimeters, the reflectivity of the plasma fluid will be sensed and sampled or recorded. This is continued until boundary 48 of the specimen is reached, and a record of the position and plasma reflectivity during the entire scan is recorded in the CPU memory. The scan data, for example, can be displayed on output device 62.

Stepping from top 47 to boundary 48 preferably is accomplished in one minute, and then the process is repeated. Head 82 raises to top 47 and reflectivity is sensed at each step to boundary 48. CPU 36, however, averages the second set of sensed reflectivity data with the first, and the scan again is accomplished in one minute. In the preferred process ten one-minute scans are made and averaged into the data, and after the last scan a plasma scan curve, such as those shown in FIGS. 21 through 29 can be generated and displayed.

It is not possible, of course, to begin measurement of the reflectivity of plasma fluid 51 until the erythrocyte or red cells have settled from the plasma to a sufficient extent to provide a representative quantity of plasma. In practice this minimum threshold is an erythrocyte one hour settling rate of about 7 millimeters.

Scanning of plasma 51 is based upon the hypothesis that while the erythrocyte cells are settling, solids, such as various types of white cells, in the plasma fluid also tend to settle. In some specimens banding or layering of white cells can be seen in the plasma. Accordingly, scanning of the plasma also tends to produce reflectivity patterns as a function of height or position below top 47. Study of the positions of features such as the position of the maximum height, dips in the reflectivity curve and the lowest value of reflectivity appear to have indicated a high degree of correlation of such scan curve features with specific inflammatory conditions.

The white cell scanning sensor 81 also is preferably adjusted during the initial red cell calibration scan of the specimen, but not to achieve a fine calibration, but to set the output of analog-to-digital converter 92b to a count of 120. Since the plasma scan does not depend upon the precise identification of the occurrence of settling, the converter 92b can operate in the middle of the conventional five volt window, and digital-to-analog converter 126b is used to set the output count at 120. Only one approximate setting is required, since currently the measured values of the sensed reflectivity are not used in a quantitative manner. It will be understood, however, that the absolute values of white cell reflectivity may be determined to be useful. The current embodiment of the apparatus determines the position of reflectivity increases and decreases relative to the separation boundary at the start of plasma scanning or top of the plasma. Once set for instrument 21, all scanned white cell curves will be scaled the same and can be compared to each other and to stored data as to inflammatory conditions.

While plasma 51 can be scanned for reflectivity using infrared radiation, radiation in other frequency ranges and transmissivity may also be suitable for scanning and correlating a characteristic of settling of the plasma with inflammatory conditions.

More particularly, it is hypothesized that different types of white cells tend to settle to differing degrees in the plasma. The bands in the plasma which are sometimes visible to the naked eye tends to support this hypothesis. It is believed that colored light in visible frequency ranges may enable identification, and possibly even quantification, of the types and settling characteristics of at least some types of white cells. Similarly, transmissivity measurements also may yield white cell typing and/or quantification data.

EXAMPLES

Using the apparatus and method of the present invention, blood specimens from various patients were studied and compared to clinical information concerning the patients.

ERYTHROCYTE SETTLING EXAMPLES

Example 1

First Trimester Pregnancy

FIGS. 11A-14D are computer print-outs of settling data for pregnant patients during various stages of pregnancy. Since pregnancy includes inflammatory conditions as an aspect of a normal pregnancy, erythrocyte settling and white cell scanning can be used to monitor pregnancy for abnormalities.

In FIGS. 11A-11D a female patient 24 years of age and in her first trimester of the pregnancy has been tested using the apparatus and method of the present invention. This same patient's white cell scan can be seen in FIG. 21.

FIG. 11A shows a one-hour Erythrocyte Settling Rate, "ESR" of 14.3 millimeters, which is a relatively low settling rate suggesting minimal inflammatory process. Sedimentation curve 121, however, appears to have a constant slope and is not very instructive or helpful in assessing the patient condition. In FIG. 11B, a divided difference or approximate settling rate curve 122 is shown. As will be seen, this curve now starts to reveal patterns in the data, not readily apparent from curve 121. In FIG. 11C a Fast Fourier Transform 123 of the settling data in curve 121 has been performed in an attempt to obtain a mathematical analysis of the distribution of frequencies making up settling curve 121. As will be seen, Fourier transform curve 123 shows patterns which are very pronounced and appear to repeat in many areas. Finally, curve 124 in FIG. 11D is a Modified Fast Fourier Transform of the data of curve 121. The analysis differs from FIG. 11C in that the first data point was eliminated. Again, however a very distinctive Fourier curve 124 results.

The use of Fourier transform curves is an attempt to facilitate pattern recognition from the accurate microcurve data captured using the present apparatus by means of computer analysis. More particularly, it is believed that a Fourier transform of the settling curve data may lend itself to computer analysis by the use of neural network data processing techniques. It is not known yet whether one or more of the divided difference curve 122, the Fast Fourier Transform curve 123, or the Modified Fast Fourier Transform curve 124 will be the most productive to use with a neural network to achieve correlations of curves with specific inflammatory conditions.

Even without the precision of computer analysis of the patterns produced by the instrument of the present invention, one can visually identify repetitive characteristics in the various curves.

Example 2

First Trimester Pregnancy

FIGS. 12A-12D are four curves 131-134 corresponding to curves 121-124. Curves 131-134 are based upon settling data taken from a 23 year old female also in her first trimester of pregnancy. As will be seen, the divided difference curves 122 and 132 are very similar, as are the Fast Fourier Transforms. The peaks 126 and 136, for example, occur in almost exactly the same position, as is true of peaks 127 and 137 in curves 124 and 134, and the shapes of these frequency distribution curves are almost identical.

Since both of these pregnancies appear from clinical testing to be entirely normal, the possibility of using the settling data, which clearly repeats, to develop a statistical model, or an envelope of data for a normal first trimester pregnancy, seems quite high. Once developed, settling rate testing can be compared against the model and abnormal pregnancies identified.

Example 3

Second Trimester Pregnancy

In FIGS. 13 and 14 a 37 year old patient in her second trimester has been tested. As will be seen the ESR has increased significantly from the first trimester pregnancies to 30.9 millimeters, but sedimentation curve 141 is very similar in overall appearance to curves 131 and 121.

In FIG. 14, however, divided difference curve 142 is considerably elevated and much more active than either of curves 132 or 122. Fourier Transform curves similarly were different but are not shown only because the types of changes are also illustrated in the patient of FIGS. 15A-15D.

Example 4

Third Trimester Pregnancy

A female patient 18 years of age and in her third trimester of pregnancy was the subject of the test of FIGS. 15A-15D. Again, sedimentation curve 143 is not very instructive, but the divided difference curve 144 clearly has recognizable differences as compared to curves 122, 132 and 142. While the ESR for the third trimester patient, 35.9 millimeters, has not increased very much from that of the second trimester (5 millimeters), the divided difference curve activity has increased substantially.

It is recognized, of course, that there are factors, such as age differences, which may affect the curves, but the high coincidence of similar curve features for curves 122 and 132 for patients of substantially the same age tends to suggest that differentiation for age also can be developed, if age affects the curves.

The Fourier curves 147 and 148 for the third trimester patient also are quite recognizably different from that of the first trimester patients. Interestingly, the maximum spikes are only slightly shifted, but the harmonic content has increased in FIGS. 15C and 15D, and patterns of secondary or harmonic frequencies are beginning to appear or be more recognizable. Again, the possibility of developing an envelope of model data as a result of the improved accuracy of the instrument and method of the present invention seems quite likely.

In FIGS. 16-20B patients with various inflammatory diseases were tested.

Example 5

Chronic Fatigue

FIGS. 16A and 16B are the settling rate curve 149 and divided difference curve 150 for a female patient 37 years of age with a chronic fatigue condition. Note that the ESR and settling curve are about the same as for the 37 year old patient of FIG. 15A. The divided difference curves 144 and 150, however, are recognizably different.

Example 6

Lung Cancer

The 59 year old female patient of FIGS. 17A and 17B has lung cancer. This patient's ESR is 57.6, which is symptomatic of substantial inflammation, and settling curve 168 and divided difference curve 169 both are quite different from the previous curves. The activity of divided difference curve 169 in the early stages of settling is very substantial. It should be noted that curves 168 and 169 are based upon 1692 data points, whereas a corresponding Williams et al. curve would be based upon 240 data points. Moreover, in the area of rapid change at the start of settling, the present instrument generates more data points than at the less significant tail portion 170 of the curve. A computer analysis of the micro-curves in the rapid falling first two-thirds of the curve would have over 1500 data points while Williams et al. data would include 160 data points. An increase in data of almost 10 times can be achieved with the instrument of the present invention, and the data selection is settling-driven, not arbitrarily taken.

Example 7

Breast Cancer

FIGS. 18A and 18B show the settling curve 180 and divided difference curve 190 for a 47 year old female patient with breast cancer. The settling rate is almost identical to the rate for the lung cancer patient, and the settling curves 180 and 168 are quite similar. The differences between the divided difference curves for these two diseases again are quite recognizable. In curve 190 there is less initial activity and even more mid-range activity than curve 169 for the lung cancer patient. Curves 169 and 190 are clearly distinguishable from each other and from the curves of the other Examples.

Examples 8 and 9

AIDS

The patients whose tests are shown in FIGS. 19A-B and 20A-B both have Acquired Immune Deficiency Syndrome (AIDS). The first patient (FIGS. 19A and 19B) is a 25 year old male without any observable complications. The second patient is a 36 year old male who also has meningitis.

The ESR for curve 178 is almost identical to curve 149 (FIG. 16A) for the patient with a chronic fatigue condition. The respective divided difference curves 150 and 179, however, are clearly different, even though physicians believe that chronic fatigue virus and the AIDS virus are broadly related.

The effect of the complicating presence of meningitis appears to increase the early activity (slope changes) in divided difference curve in FIG. 20B. The settling curve 176 also has a somewhat steeper slope which is reflected in the elevated divided difference curve. Again, the number of data points used to generate the first two-thirds of curves 176 and 177 will be approximately 8 to 10 times the number employed in the prior art.

PLASMA SCAN EXAMPLES

FIGS. 21-29 are examples of computer generated displays of plasma or white cell scans using the apparatus and process of the present invention.

It was anticipated that there also would be variations in the plasma scan curves from individual to individual. Testing to date suggests that the possibility of developing envelopes of plasma scan curves, which can be used alone or with settling data, and which have a very high degree of correlation to specific inflammatory conditions, seems high.

In FIGS. 21-24 are scans of the pregnant patients of Examples 1, 2, 3 and 4. In FIGS. 21 and 22 both patients are in their first trimester, and they correspond to Examples 1 and 2, respectively. As will be seen by comparing these scans the overall shape of scans 151 and 152 is very similar. Both have peaks 153 and 154 followed by a dip which ends in shoulders 155 and 156. After the shoulders the curves drop dramatically at 157 and 158 to a minimum reflectivity (higher cell density proximate separation boundary 48) at 159 and 160. Moreover, the relative spacing between these features has a high degree of consistency.

Both of these patients are having a normal pregnancy free of inflammatory complications.

FIG. 23 shows the scan of the 37 year old patient in the second trimester of her pregnancy of Example 3. As compared to curves 151 and 152, this curve 163 has a peak 164 which is much more closely followed by a very slight dip and shoulder 165. Curve 163 then descends rapidly at 166 to an almost constant minimum or tail 167, which is longer by reason of the greater erythrocyte settling and more plasma to scan than for curves 151 and 152.

In FIG. 24, white cell scan 171 is for the 18 year old pregnant patient in her third trimester of Example 4. The peak 172, dip and shoulder 173 structure has increased as compared to curve 163, but still can be seen to be less than that of curves 151 and 152. Again, after shoulder 173 there is a rapid drop 174 followed by a nearly level long tail 175.

Thus, white cell scans 151, 152, 163 and 171 show both a characteristic pregnancy curve, similarities and repeating structures for similar lengths of pregnancies and changes which differentiate the length of pregnancy. All of these patients are experiencing normal pregnancies, but if they did have an inflammatory disease complication, the white cell scans would be significantly altered.

In FIG. 25, for example, the white cell scan 181 for the 37 year old female patient of Example 5 with a chronic fatigue condition is shown. The curve peaks at 182 and then dips slightly at 183. As will be seen, however, there is no shoulder after dip 183, nor is there a rapid drop to a minimum. Instead, dip 183 is the minimum and the curve continues with a gradually rising long tail 184.

Comparing curve 181 with curve 171 makes it apparent that the inflammatory conditions of the two patients are radically different. The one-hour erythrocyte settling rate for the chronic fatigue patient whose scan is shown by curve 181 was 37.4 millimeters, while the one-hour settling rate for the third trimester pregnancy was 35.9 millimeters. Clearly, the erythrocyte settling rate alone is not a tool capable of distinguishing between these patients, but the white cell scan is.

In FIG. 26, scan 186 is for the 59 year old female patient with lung cancer of Example 6. Again, there is an initial peak 187, dip 188 and shoulder 189 structure. The spacing of these features is somewhat greater than for pregnant patients, and while there is a drop 190, it is relatively short. Curve 186 also includes a long tail 191 with a rise or shoulder 192 which is believed to be significant and is not present in either the pregnant or chronic fatigue patients.

FIG. 27 shows a scan for the 47 year old female patient of Example 7 who has breast cancer. Curve 195 includes a peak 196 and a shoulder 197, followed by a very short drop 198, an immediate rise 199 and a long declining tail 200. Thus, significantly different features can be found between lung cancer scan 186 and breast cancer scan 195.

Finally, FIGS. 28 and 29 are plasma scan curves for patients with AIDS. Curve 301 is for the male patient who is 36 years old and curve 302 is for the male patient who is 25 years old. As will be seen in both curves, there is an initial peak 303 and 304, but the peak is followed by greatly elongated dips or flat sections 305 and 306, which appears to terminate in very slight shoulders 307 and 308. After the shoulders 307 and 308 the tails 309 and 310 tend to remain level or even rise somewhat.

Interesting similarities can be seen between AIDS scan 301 and chronic fatigue scan 181. This is not too surprising since both are believed to be viral-based with numerous similarities. When the divided difference curves 150 and 190 are compared, however, these two patients can be clearly distinguished.

Thus, the potential for use of a combination of erythrocyte data and white cell scans to enhance diagnoses also is apparent.

REFLECTIVITY MEASUREMENTS

Example 10

Pregnancy First Trimester

FIG. 30 is a computer display curve 401 of reflectivity measurements made immediately (15 milliseconds) after each step during a settling rate test for a pregnant patient in her first trimester. This patient is not the patient of Examples 1 or 2. In curve 401 the reflectivity measured at the zero abscissa point is at the start of settling. This patient was 24 years old and her ESR was 35.2 millimeters, which is high for a first trimester patient.

Example 11

Breast Cancer

In FIG. 31 a reflectivity measurement curve 402 for a female patient 39 years old with breast cancer and an ESR of 51.4 millimeters is shown. This is not the same patient as Example 7.

Comparing curves 401 and 402 a clearly recognizable pattern difference in the measured reflectivity is discernable. The ability of the present instrument to take steps when settling occurs, to be settling-driven, rather than time-driven, provides, it is believed, data in which the reflectivity measurements are more capable of being compared for meaningful differences.

Again, reflectivity measurements are believed to be useful alone, or with settling data and/or plasma scans, to help in the correlation of curve patterns with inflammatory conditions.

What is claimed is:

1. In a process for sensing the settling of erythrocyte cells including the steps of, settling erythrocyte cells of a test specimen of blood in a settling tube, sensing a characteristic of said specimen indicative of the location of a separation boundary between said erythrocyte cells and plasma fluid in said specimen, said sensing occurring at a position proximate to said separation boundary and said characteristic changing with erythrocyte settling, and sampling the sensed characteristic periodically to provide data useful in determining the position of said separation boundary during settling, the improvement in said process comprising:

said step of sensing a characteristic of said specimen being accomplished by irradiating said specimen with irradiation having a wavelength in at least one of the visible and infrared ranges, and sensing changes in the reflectivity of said specimen to said irradiation at a sensing rate greater than the rate of occurrence of changes in said reflectivity; and said step of sampling said sensed characteristic occurring in response to sensing of said reflectivity at times determined by the occurrence of a change in said sensed reflectivity.

2. The process as defined in claim 1 wherein, said step of sampling said sensed characteristic occurs when said sensed characteristic exceeds between about 5 and about 20 percent of a calibrated level for said sensed characteristic.

3. The process as defined in claim 1 wherein, said sensing step is accomplished at a sensing rate of at least about 50 times as often as the frequency of occurrence of a change in said characteristic of sufficient magnitude to be related to settling.

4. The process as defined in claim 1 wherein, said sensing step is accomplished at least as often as once every 0.01 seconds; and said sampling step is accomplished when said characteristic exceeds a threshold amount sufficiently above a calibrated level to indicate the occurrence of a significant settling of said erythrocyte cells.

5. The process as defined in claim 1 wherein, said sensing step and said sampling step are accomplished by sensing at a first position until said sampling step is performed, and after said sampling step, commencing sensing at a second position below said first position by an amount less than 0.10 millimeters until said sampling step is performed again.

6. The process as defined in claim 1 wherein, said irradiating is accomplished by transmitting pulses of irradiation.

7. The process as defined in claim 1 wherein, said sensing step is accomplished by irradiating said specimen with infrared radiation.

8. In a process useful in measuring the settling of erythrocytes including the steps of, settling a test specimen of blood in a settling tube, and sensing the height of a separation boundary between erythrocyte cells and plasma fluid with a sensing means as said separation boundary lowers to generate an output, the improvement of said process comprising:

said sensing is accomplished by sensing the reflectivity of said specimen to irradiation, and sampling sensed reflectivity data in response to a change in the reflectivity.

9. The process as defined in claim 8 wherein, said sensing step occurs at a rate of at least about once every 0.01 seconds.

10. The process as defined in claim 9 wherein, said reflectivity is detected at and immediately below said separation boundary.

11. The process as defined in claim 8 wherein, said sensing is accomplished using at least one of static and pulsed infrared irradiation.

12. The process as defined in claim 8, and the steps of:

during said sensing obtaining time data and corresponding position data as to the location of said separation boundary; and comparing said time data and said position data of said separation boundary of said test specimen with at least one set of corresponding time data and position data for a control specimen of blood for a comparable time period.

13. The process as defined in claim 12 wherein, said comparing step includes the step of identifying repetitive patterns in data from said test specimen which are substantially the same as repetitive patterns in said data from settling of said control specimen.

14. The process as defined in claim 8, and the step of: prior to said sensing and said sampling, periodically measuring a characteristic of said specimen at a fixed location below said separation boundary while said separation boundary settles toward said fixed location.

15. The process as defined in claim 14 wherein: said step of periodically measuring is accomplished by measuring the reflectivity of said specimen to irradiation at a fixed location which initially is about 2.5 millimeters below said separation boundary, and continuing periodic measuring until said separation boundary reaches said fixed location.

16. The process as defined in claim 15 wherein, said measuring step is accomplished at least as often as once per second.

17. In a process useful in sensing the settling of erythrocyte cells including the steps of settling erythrocyte cells of a test specimen of blood in a settling tube, and tracking the settling of a separation boundary between said erythrocyte cells and plasma fluid by periodically sensing a characteristic of said specimen indicating settling of said erythrocyte cells proximate said separation boundary, the improvement in said process comprising: said sensing being accomplished by sensing reflectivity of said specimen to at least one of visible light irradiation and infrared irradiation at a sensing rate greater than the rate of occurrence of significant changes in said characteristic; and periodically sampling said sensed characteristic at sampling times determined by the occurrence of a change in said sensed characteristic over a predetermined threshold.

18. In a process useful in sensing the settling of erythrocyte cells including the steps of settling erythrocyte cells of a test specimen of blood in a settling tube, and tracking the height in said settling tube of a separation boundary between said erythrocyte cells and plasma fluid by periodically sensing a characteristic of said specimen proximate and separation boundary, the improvement in said process comprising: periodically sampling reflectivity of said specimen immediately below said separation boundary to provide tracking data at sequential positions down said settling tube having a height difference between said sequential positions of not more than about 0.1 millimeter; and periodically sampling said sensed reflectivity at a sampling rate of not less than about twice per second.

19. The process as defined in claim 18, wherein said periodically sampling is accomplished at positions having a height difference of not more than 0.068 millimeters; and said periodically sampling is accomplished at a sampling rate of not less than 20 times per second.

20. In a process useful in sensing the settling rate of erythrocyte cells including the steps of settling erythrocyte cells of a test specimen of blood in a settling tube, and sensing the rate of settling of said erythrocyte cells over a time period by using a beam of radiation to follow a separation boundary between said erythrocyte cells and plasma fluid in said test specimen, the improvement in said process comprising: said sensing step being accomplished by sensing changes in a characteristic of said test specimen in a tracking zone from a position proximate to and below said separation boundary up to a position at said separation boundary.

21. The process as defined in claim 20 wherein, said sensing is accomplished by sensing changes in the reflectivity of a beam of static radiation off of a portion of said specimen having said erythrocyte cells.

22. The process as defined in claim 21 wherein, said sensing is accomplished by directing an infrared beam of radiation against said erythrocyte cells proximate and below said boundary and sensing changes in reflectivity of said infrared beam.

23. The process as defined in claim 22 wherein, the sensing step is accomplished by moving said beam of infrared radiation down said settling tube as said separation boundary moves down said settling tube by displacing said beam downwardly by a predetermined fixed step each time said reflectivity increases above a predetermined threshold, and determining an approximate settling rate by dividing the change in position of said beam by the change in time between two sequentially spacially adjacent fixed steps.

24. The process as defined in claim 20 wherein, said sensing is accomplished by measuring an amount of reflectivity of said erythrocyte cells substantially immediately after a measurable change in the height of said separation boundary occurs.

25. In a process useful in sensing the settling of erythrocyte cells including the step of settling erythrocyte cells of a test specimen of blood in a settling tube, the improvement in said process comprising: sensing the reflectivity of said test specimen in a fixed sensing zone at a position which initially is significantly below a separation boundary between said erythrocyte cells and plasma fluid until said separation boundary reaches said fixed sensing zone, and thereafter sampling said reflectivity upon sensing of a significant change therein.

26. The process as defined in claim 25 wherein, said fixed sensing zone is initially positioned at least about 2 millimeters below said separation boundary.

27. The process as defined in claim 25 wherein, said reflectivity being sensed during said sensing is sampled at least as often as once every second.

28. The process as defined in claim 27 wherein, said reflectivity being sensed during said sensing is sampled at least as often as once every 0.01 seconds.

29. The process as defined in claim 25, and after said separation boundary reaches said fixed sensing zone, moving said fixed sensing zone to a new fixed sensing zone below said separation boundary by a significant amount, and sensing said reflectivity at said new fixed sensing zone and sampling the sensed reflectivity upon sensing a significant change in reflectivity.

30. The process as defined in claim 25 wherein, said sensing is accomplished by irradiating said specimen with infrared radiation and sensing the reflectivity of said specimen to said radiation.

* * * * *

UNITED STATES PATENT AND TRADEMARK OFFICE
CERTIFICATE OF CORRECTION

PATENT NO. :   5,328,822

DATED      :   July 12, 1994

INVENTOR(S) :   David K. McKinney, et al.

It is certified that error appears in the above-identified patent and that said Letters Patent is hereby corrected as shown below:

Column 16, line 6, after "set to" insert
--be 150 counts above the $V_{set}$, namely at 3.284 volts,--.

Signed and Sealed this

Eleventh Day of October, 1994

Attest:

BRUCE LEHMAN

Attesting Officer   Commissioner of Patents and Trademarks